United States Patent
Prestwich et al.

(10) Patent No.: US 8,324,184 B2
(45) Date of Patent: Dec. 4, 2012

(54) ANTI-ADHESION COMPOSITES AND METHODS OF USE THEREOF

(75) Inventors: Glenn D. Prestwich, Salt Lake City, UT (US); Kelly R. Kirker, Bozeman, MT (US); Steven D. Gray, Salt Lake City, UT (US); Janice Gray, legal representative, Salt Lake City, UT (US); Xiao Zheng Shu, Dublin, CA (US); Hao Li, San Diego, CA (US); Yanchun Liu, Nashville, TN (US)

(73) Assignee: University of Utah Research Foundation, Salt Lake City, UT (US)

( * ) Notice: Subject to any disclaimer, the term of this patent is extended or adjusted under 35 U.S.C. 154(b) by 1424 days.

(21) Appl. No.: 10/556,693

(22) PCT Filed: May 13, 2004

(86) PCT No.: PCT/US2004/014965
§ 371 (c)(1),
(2), (4) Date: Dec. 3, 2008

(87) PCT Pub. No.: WO2005/000402
PCT Pub. Date: Jan. 6, 2005

(65) Prior Publication Data
US 2009/0124540 A1 May 14, 2009

Related U.S. Application Data

(60) Provisional application No. 60/471,482, filed on May 15, 2003.

(51) Int. Cl.
*A61K 31/728* (2006.01)
*A61K 31/717* (2006.01)
*A61K 31/405* (2006.01)
*A61K 9/70* (2006.01)
*A61K 9/00* (2006.01)

(52) U.S. Cl. ............ 514/54; 514/57; 514/411; 424/422; 424/443; 424/488

(58) Field of Classification Search ............... 514/54, 514/57, 411; 424/422, 443, 488
See application file for complete search history.

(56) References Cited

U.S. PATENT DOCUMENTS

| | | | |
|---|---|---|---|
| 5,580,923 A | 12/1996 | Yeung et al. | |
| 6,063,396 A | 5/2000 | Kelleher | |
| 6,235,726 B1 | 5/2001 | Burns et al. | |
| 6,534,591 B2 | 3/2003 | Rhee et al. | |
| 6,548,081 B2 | 4/2003 | Sadozai et al. | |
| 6,551,610 B2 | 4/2003 | Shalaby et al. | |

FOREIGN PATENT DOCUMENTS

| | | |
|---|---|---|
| WO | WO 01/60868 A1 | 8/2001 |
| WO | WO 2004/037164 A2 | 5/2004 |

OTHER PUBLICATIONS

Park et al. Biomaterials, 2003, 24, p. 893-900, Available online Dec. 19, 2002.*
Lutolf et al. Bioconjugate Chem., 2001, 12, p. 1051-1056.*
Shu et al. Biomacromolecules, 2002, 3, p. 1304-1311, Published on Web Sep. 27, 2002.*
Akima, K. et al., "Evaluation of antitumor activities of hyaluronate binding antitumor drugs", *J. Drug Targeting*, 4:1-8 (1996).
Arnold, P. B. et al., "Evaluation of resorbable barriers for preventing surgical adhesions", *Fertility and Sterility*, 73:157-161 (2000).
Belluco, C. et al., "Prevention of postsurgical adhesions with an autocrosslinked hyaluronan derivative gel", *Journal of Surgical Research*, 100:217-221 (2001).
Burns, J. W. et al., "Prevention of tissue injury and postsurgical adhesions by precoating tissues with hyaluronic acid solutions", *Journal of Surgical Research*, 59:644-652 (1995).
Burns, J. W. et al., "A Hyaluronate Based Gel for the Prevention of Postsurgical Adhesions: Evaluation in Two Animal Species", *Fertility and Sterility*, 66(5):814-821 (1995).
Burns, J. W. et al., "Preclinical evaluation of Seprafilm bioresorbable membrane", *Eur. J. Surg.*, 577(Suppl):40-8 (1997).
di Zerega, G. S., and Campeau, J. D., "Peritoneal repair and post-surgical adhesion formation", *Hum. Reprod. Update* 7:547-555 (2001).
Ferland, R., Mulani, D., and Campbell, P., "Evaluation of a sprayable polyethylene glycol adhesion barrier in a porcine efficacy model", *Hum. Reprod.* 16:18-23 (2001).
Gray, S. et al. "The effect of mitomycin on extracellular matrix proteins in a rat wound model", *Laryngoscope*, in review (2002).
Haney, A. F., and Doty, E., "A barrier composed of chemically cross-linked hyaluronic acid (Incert) reduces postoperative adhesion formation", *Fertil. Steril.* 70:145-151 (1998).
Hartnick, C. et al., "Topical mitomycin application after laryngotracheal reconstruction: a randomized double-blind, placebo-controlled trial", *Arch. Otolaryngol. Head Neck Surg.*, 127:1260-1264 (2001).
Hooker, G. D. et al. "Prevention of adhesion formation with use of sodium hyaluronate-based bioresorbable membrane in a rat model of ventral hernia repair with polypropylene mesh-A randomized, controlled study", *Surgery* 125:211-216 (1999).
Johns, D. B. et al., "Reduction of adhesion with formation by postoperative administration of ionically cross-linked hyaluronic acid", *Fertility and Sterility*, 68(1):37-42 (1997).
Johns, D. B. et al., "Reduction of postsurgical adhesions with Intergel (R) adhesion prevention solution: a multicenter study of safety and efficacy after conservative gynecologic surgery", *Fertility and Sterility*, 76(3):595-604 (2001).
Jones, K.H. et al., "An improved method to determine cell viability by simultaneous staining with fluorescein diacetate-propidium iodide", *The Journal of Histochemistry and Cytochemistry*, 33(1):77-79 (1985).

(Continued)

*Primary Examiner* — Shaojia Anna Jiang
*Assistant Examiner* — Jonathan S Lau
(74) *Attorney, Agent, or Firm* — Gardner Groff Greenwald & Villanueva, P.C.

(57) ABSTRACT

Described herein are composites that inhibit or reduce adhesion between two or more tissues. Also described herein are methods of using the composites.

40 Claims, 12 Drawing Sheets

OTHER PUBLICATIONS

Kirker, K. et al., "Glycosaminoglycan hydrogel films as bio-interactive dressings for wound healing", *Biomaterials*, 23:3661-3671 (2002).

Kirker, K. et al., "Glycosaminoglycan hydrogels as supplemental wound dressings for donor sites", *Journal of Burn Care and Rehabilitation*, 25:276-286 (2004).

Li, H. et al., "Synthesis and biological evaluation of a cross-linked hyaluronan-mitomycin C hydrogel", *Biomacromolecules*, 5(3):895-902 (2004).

Liu, Y. et al., "Crosslinked hyaluronan hydrogels containing mitomycin C reduce postoperative abdominal adhesions", *Fertility and Sterility*, 83(Suppl. 1):1275-1283 (2005).

Macky, T. et al., "Synthesis, pharmacokinetics, efficacy, and rat retinal toxicity of a novel mitomycin C-triamcinolone acetonide conjugate", *J. Med. Chem.*, 45:1122-1127 (2002).

Osada, H., Takahashi, K., Fujii, T. K., Tsunoda, I., and Satoh, K., "The effect of cross-linked hyaluronate hydrogel on the reduction of post-surgical adhesion reformation in rabbits", *J. Int. Med. Res.* 27:233-241 (1999).

Pouyani, T., "Functionalized Derivatives of Hyaluronic Acid Oligosaccharides: Drug Carriers and Novel Biomaterials", *Bioconjugate Chemistry*, 5:339-347 (1994).

Prestwich, G. D. (2001) Biomaterials from chemically-modified hyaluronan, *Glycoforum* http://glycolorum.gr.jp/science/hyaluronan/HA18/HA18E.html.

Rahal, A., Peloquin, L., and Ahmarani, C., "Mitomycin C in sinus surgery: preliminary results in a rabbit model", *J. Otolaryngol.* 30:1-5 (2001).

Shu, X.Z. et al., "Attachment and spreading of fibroblasts on an RGD peptide-modified injectable hyaluronan hydrogel", *Journal of Biomedical Materials Research*, 68A:365-375 (2004).

Vercruysse, K.P. et al., "Synthesis and in vitro degradation of new polyvalent hydrazide cross-linked hydrogels of hyaluronic acid", *Bioconjugate Chemistry*, 8:686-694 (1997).

\* cited by examiner

ANTI-ADHESION COMPOSITES AND METHODS OF USE THEREOF

CROSS REFERENCE TO RELATED APPLICATIONS

This application claims the benefit of U.S. provisional application Ser. Nos. 60/471,482, filed May 15, 2003. This application is hereby incorporated by this reference in its entirety for all of its teachings.

ACKNOWLEDGEMENTS

The research leading to this invention was funded in part by the National Institutes of Health, Grant No. NIH DC04336. The U.S. Government may have certain rights in this invention.

BACKGROUND

Adhesions are the formation of fibrous attachments between two apposing surfaces, and are often formed during the dynamic process of healing of the incision and tissue trauma after surgery. The initiation of the adhesion begins with the formation of a fibrin matrix. The ischemic conditions caused by surgery prevent fibrinolytic activity to dissolve the matrix, and the fibrin persists. Wound repair cells then turn the matrix into an organized adhesion, often having a vascular supply and neuronal elements.

Adhesions are a particular problem in gastrointestinal and gynecological surgery, leading to post-operative bowel obstruction, infertility, and chronic pelvic pain. The barrier method of reducing post-surgical adhesions is most commonly used (Arnold, P. B., Green, C. W., Foresman, P. A, and Rodeheaver, G. T. (2000) "Evaluation of resorbable barriers for preventing surgical adhesions"*Fert Steril* 73, 157-161; Osada, H., Takahashi, K., Fujii, T. K., Tsunoda, I., and Satoh, K. (1999) "The effect of cross-linked hyaluronate hydrogel on the reduction of post-surgical adhesion reformation in rabbits" *J Int Med Res* 27, 233-241). For example, Seprafilm™ (Genzyme) is a bioresorbable membrane prepared from hyaluronan (HA) and carboxymethyl cellulose (CMC) that reduces adhesions. Seprafilm, however, has poor handling properties and a short residence time that contributes to loss of efficacy. An internally esterified form of HA (ACP™ gel, Fidia Advanced Biopolymers) and a 0.5% ferric iron jonically crosslinked HA gel (Intergel™, Lifecore Biomedical) are newer barrier materials which do not accelerate healing of the incisions. Described herein are composites that inhibit or reduce adhesion between two or more tissues.

SUMMARY OF EMBODIMENTS

Described herein are composites that inhibit or reduce adhesion between two or more tissues and kits used to produce the composite. Also described herein are methods of using the composites.

The advantages of the invention will be set forth in part in the description which follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE DRAWINGS

The accompanying drawings, which are incorporated in and constitute a part of this specification, illustrate several aspects described below.

DETAILED DESCRIPTION

Figure 1:
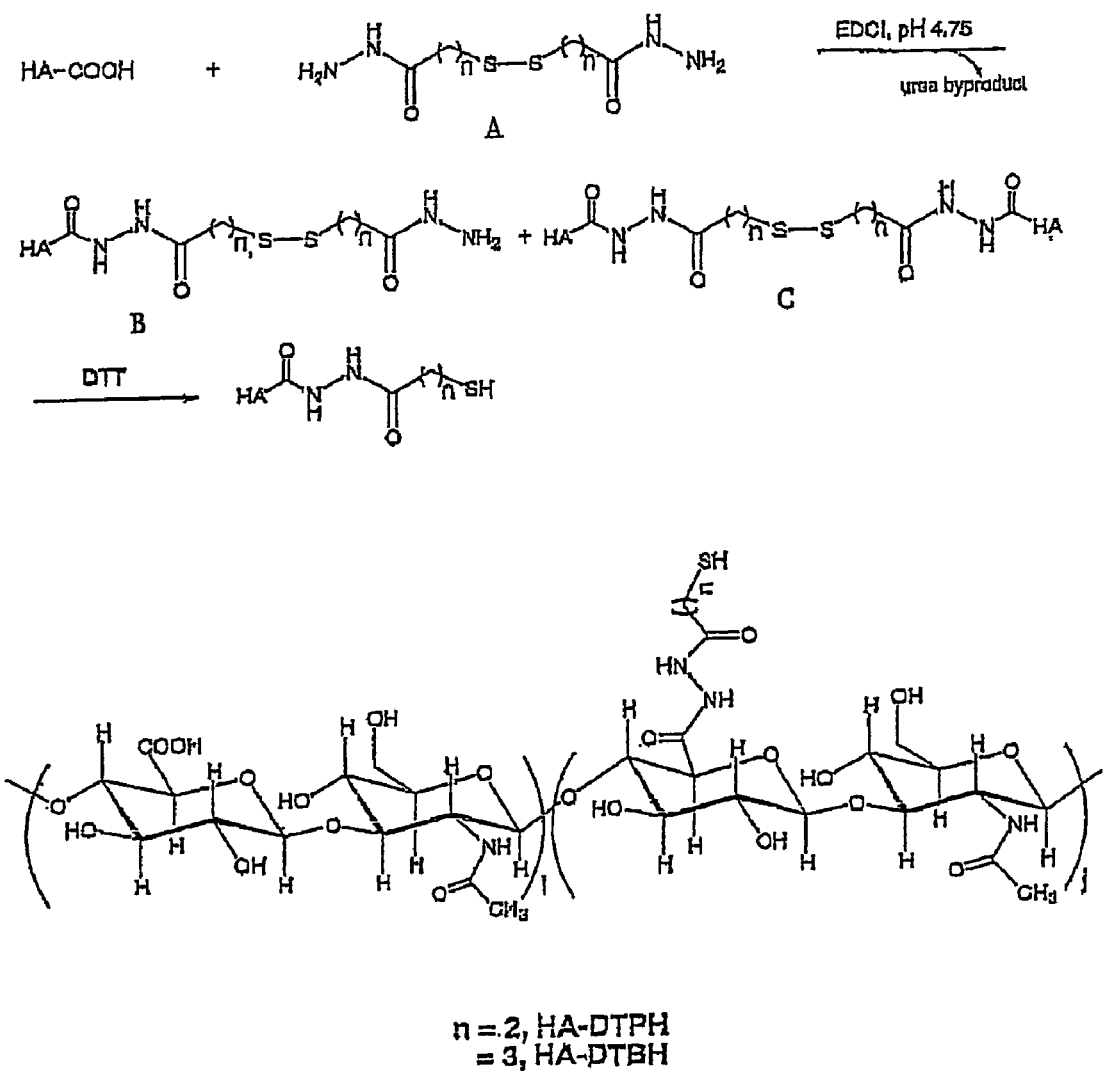
FIG. 1 shows the reaction scheme for producing HA-thiolated derivatives.

Before the present composites, compositions, and/or methods are disclosed and described, it is to be understood that the aspects described below are not limited to specific compounds, synthetic methods, or uses as such may, of course, vary. It is also to be understood that the terminology used herein is for the purpose of describing particular aspects only and is not intended to be limiting.

In this specification and in the claims that follow, reference will be made to a number of terms that shall be defined to have the following meanings:

It must be noted that, as used in the specification and the appended claims, the singular forms "a," "an," and "the" include plural referents unless the context clearly dictates otherwise. Thus, for example, reference to "a pharmaceutical carrier" includes mixtures of two or more such carriers, and the like.

"Optional" or "optionally" means that the subsequently described event or circumstance can or cannot occur, and that the description includes instances where the event or circumstance occurs and instances where it does not. For example, the phrase "optionally substituted lower alkyl" means that the lower alkyl group can or can not be substituted and that the description includes both unsubstituted lower alkyl and lower alkyl where there is substitution.

Ranges may be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

References in the specification and concluding claims to parts by weight, of a particular element or component in a composition or article, denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent of a component, unless specifically stated to the contrary, is based on the total weight of the formulation or composition in which the component is included.

A residue of a chemical species, as used in the specification and concluding claims, refers to the moiety that is the resulting product of the chemical species in a particular reaction scheme or subsequent formulation or chemical product, regardless of whether the moiety is actually obtained from the chemical species. For example, a polysaccharide that contains at least one —COOH group can be represented by the formula Y—COOH, where Y is the remainder (i.e., residue) of the polysaccharide molecule.

Variables such as $R^3$-$R^5$, $R^7$, $R^8$, L, G, M, U, V, X, Y, and Z used throughout the application are the same variables as previously defined unless stated to the contrary.

The term "alkyl group" as used herein is a branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, decyl, tetradecyl, hexadecyl, eicosyl, tetracosyl and the like. A "lower alkyl" group is an alkyl group containing from one to six carbon atoms.

The term "polyalkylene group" as used herein is a group having two or more $CH_2$ groups linked to one another. The polyalkylene group can be represented by the formula —$(CH_2)_n$—, where n is an integer of from 2 to 25.

The term "polyether group" as used herein is a group having the formula —$[(CHR)_nO]_m$—, where R is hydrogen or a lower alkyl group, n is an integer of from 1 to 20, and m is an integer of from 1 to 100. Examples of polyether groups include, polyethylene oxide, polypropylene oxide, and polybutylene oxide.

The term "polythioether group" as used herein is a group having the formula —$[(CHR)_nS]_m$—, where R is hydrogen or a lower alkyl group, n is an integer of from 1 to 20, and m is an integer of from 1 to 100.

The term "polyimino group" as used herein is a group having the formula —$[(CHR)_nNR]_m$—, where each R is, independently, hydrogen or a lower alkyl group, n is an integer of from 1 to 20, and m is an integer of from 1 to 100.

The term "polyester group" as used herein is a group that is produced by the reaction between a compound having at least two carboxylic acid groups with a compound having at least two hydroxyl groups.

The term "polyamide group" as used herein is a group that is produced by the reaction between a compound having at least two carboxylic acid groups with a compound having at least two unsubstituted or monosubstituted amino groups.

The term "aryl group" as used herein is any carbon-based aromatic group including, but not limited to, benzene, naphthalene, etc. The term "aromatic" also includes "heteroaryl group," which is defined as an aromatic group that has at least one heteroatom incorporated within the ring of the aromatic group. Examples of heteroatoms include, but are not limited to, nitrogen, oxygen, sulfur, and phosphorus. The aryl group can be substituted or unsubstituted. The aryl group can be substituted with one or more groups including, but not limited to, alkyl, alkynyl, alkenyl, aryl, halide, nitro, amino, ester, ketone, aldehyde, hydroxy, carboxylic acid, or alkoxy.

I. Anti-Adhesion Composites

In one aspect, described herein are composites comprising (1) a first compound comprising a first anti-adhesion compound covalently bonded to a first anti-adhesion support and (2) a first prohealing compound.

The term "anti-adhesion compound" as referred to herein is defined as any compound that prevents cell attachment, cell spreading, cell growth, cell division, cell migration, or cell proliferation. In one aspect, compounds that induce apoptosis, arrest the cell cycle, inhibit cell division, and stop cell motility can be used as the anti-adhesion compound. Examples of anti-adhesion compounds include, but are not limited to anti-cancer drugs, anti-proliferative drugs, PKC inhibitors, ERK or MAPK inhibitors, cdc inhibitors, antimitotics such as colchicine or taxol, DNA intercalators such as adriamycin or camptothecin, or inhibitors of PI3 kinase such as worttnannin or LY294002. In one aspect, the anti-adhesion compound is a DNA-reactive compound such as mitomycin C. In another aspect, any of the oligonucleotides disclosed in U.S. Pat. No. 6,551,610, which is incorporated by reference in its entirety, can be used as the anti-adhesion compound. In another aspect, any of the anti-inflammatory drugs described below can be the anti-adhesyion compound. Examples of anti-inflammatory compounds include, but are not limited to, methyl prednisone, low dose aspirin, medroxy progesterone acetate, and leuprolide acetate.

The term "anti-adhesion support" as referred to herein is defined as any compound that is capable of forming a covalent bond with the anti-adhesion compound that that does not adhere to, spread, or proliferate cells. In one aspect, the anti-adhesion support is a hydrophilic, natural or synthetic polymer. Any of the polyanionic polysaccharides disclosed in U.S. Pat. No. 6,521,223, which is incorporated by reference in its entirety, can be used as the anti-adhesion support. Examples of polyanionic polysaccharides include, but are not limited to, hyaluronan, sodium hyaluronate, potassium hyaluronate, magnesium hyaluronate, calcium hyaluronate, carboxymethylcellulose, carboxymethyl amylose, or a mixture of hyaluronic acid and carboxymethylcellulose.

The formation of the first compound involves reacting the anti-adhesion compound with the anti-adhesion support to form a new covalent bond. In one aspect, the anti-adhesion compound possesses a group that is capable of reacting with the anti-adhesion support. The group present on the anti-adhesion compound that can react with the anti-adhesion support can be naturally-occurring or the anti-adhesion compound can be chemically modified to add such a group. In another aspect, the anti-adhesion support can be chemically modified so that it is more reactive with the anti-adhesion compound.

In one aspect, the first compound can be formed by crosslinking the anti-adhesion compound with the anti-adhesion support. In one aspect, the anti-adhesion compound and the anti-adhesion support each possess at least one hydrazide group, which then can react with a crosslinker having at least two hydrazide-reactive groups. Examples of hydrazide-reactive groups include, but are not limited to, a carboxylic acid or the salt or ester thereof, an aldehyde group, or a keto group. Any of the crosslinkers disclosed in international publication no. WO 02/06373 A1, which is incorporated by reference in its entirety, can be used in this aspect. In one aspect, the crosslinker is a polyethylene glycol dialdehyde.

In another aspect, the first compound can be formed by the oxidative coupling of the anti-adhesion compound with the anti-adhesion support. In one aspect, when the anti-adhesion compound and the anti-adhesion support each possess a thiol group, the anti-adhesion compound and the anti-adhesion support can react with one another in the presence of an oxidant to form a new disulfide bond. In one aspect, the reaction between the anti-adhesion compound and the anti-adhesion support can be conducted in the presence of any gas that contains oxygen. In one aspect, the oxidant is air. This aspect also contemplates the addition of a second oxidant to expedite the reaction. In another aspect, the reaction can be performed under an inert atmosphere (i.e., oxygen free), and an oxidant is added to the reaction. Examples of oxidants useful in this method include, but are not limited to, molecular iodine, hydrogen peroxide, alkyl hydroperoxides, peroxy acids, dialkyl sulfoxides, high valent metals such as $Co^{+3}$ and $Ce^{+4}$, metal oxides of manganese, lead, and chromium, and halogen transfer agents. The oxidants disclosed in Capozzi, G.; Modena, G. In *The Chemistry of the Thiol Group Part II*; Patai, S., Ed.; Wiley: New York, 1974; pp 785-839, which is incorporated by reference in its entirety, are useful in the methods described herein.

The reaction between the anti-adhesion compound and the anti-adhesion support can be conducted in a buffer solution that is slightly basic. The amount of the anti-adhesion compound relative the amount of the anti-adhesion support can vary. In one aspect, the volume ratio of the anti-adhesion compound to the anti-adhesion support is from 99:1, 90:10, 80:20, 70:30, 60:40, 50:50, 40:60, 30:70, 20:80, 10:90, or 1:99. In one aspect, the anti-adhesion compound and the anti-adhesion support react in air and are allowed to dry at room temperature. In this aspect, the dried material can be exposed to a second oxidant, such as hydrogen peroxide. The resultant compound can then be rinsed with water to remove any unreacted anti-adhesion compound, anti-adhesion support, and any unused oxidant. One advantage of preparing the first compound via the oxidative coupling methodology described herein is that coupling can occur in an aqueous media under physiologically benign conditions without the necessity of additional crosslinking reagents.

In one aspect, the anti-adhesion support has been chemically modified so that it has the formula IIII.

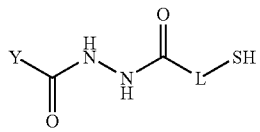

III wherein
Y can be a residue of the anti-adhesion support, and
L can be a polyalkylene group, a polyether group, a polyamide group, a polyimino group, a polyester, an aryl group, or a polythioether group.

In one aspect, L in formula III can be $CH_2CH_2$ or $CH_2CH_2CH_2$. In one aspect, the residue of the anti-adhesion support in formula III is carboxymethylcellulose, hyaluronan, or a chemically modified-derivative of hyaluronan.

FIG. 1 depicts one aspect of the method described above for producing the anti-adhesion support having the formula III, where Y is hyaluronan. The first step involves reacting a macromolecule having the formula Y—COOH with the dihydrazide/disulfide compound having the formula A. The reaction is performed in the presence of a condensing agent. A condensing agent is any compound that facilitates the reaction between the dihydrazide group of compound A and the COOH group on the macromolecule. In one aspect, the condensing agent is a carbodiimide, including, but not limited to, 1-ethyl-3-[3-(dimethylamino)propyl]-carbodiimide (EDCI). As depicted in FIG. 1, a mixture of products (B and C) are produced after the first step. The disulfide bond in compounds B and C is cleaved with a reducing agent. In one aspect, the reducing agent is dithiothreitol. Cleavage of the disulfide bonds in compounds B and C produces the anti-adhesion support having the formula III.

The first compounds produced using the methods described above have at least one fragment comprising the formula VI

VI wherein
Y can be a residue of the anti-adhesion support; and
G can be a residue of the anti-adhesion compound.

The term "fragment" as used herein refers to the entire molecule itself or a portion or segment of a larger molecule. For example, Y in formula VI may be high molecular weight hyaluronan that is crosslinked by a disulfide linkage with the anti-adhesion compound to produce the first compound. Alternatively, the first compound may have multiple disulfide linkages. In this aspect, the first compound has at a minimum one unit depicted in formula VI, which represents at least one disulfide linkage as the result of at least one anti-adhesion compound that reacted with at least one anti-adhesion support via oxidation.

In one aspect, the fragment having the formula VI has the formula VIII

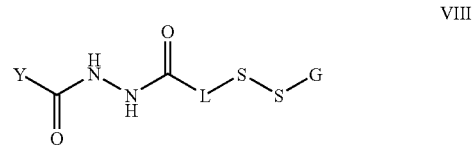

VIII wherein
Y can be a residue of the anti-adhesion support;
L can be a polyalkylene group, a polyether group, a polyamide group, a polyimino group, an aryl group, a polyester, or a polythioether group; and
G can be a residue of an anti-adhesion compound.

In one aspect, L in formula VIII can be a polyalkylene group. In another aspect, L in formula III can be a $C_1$ to $C_{20}$ polyalkylene group. In another aspect, L in formula I can be $CH_2CH_2$ or $CH_2CH_2CH_2$. In another aspect, Y can be a residue of carboxymethylcellulose, hyaluronan, or a chemically modified-derivative of hyaluronan.

In another aspect, the first compound is produced by reacting the anti-adhesion support having at least one SH group with at least one anti-adhesion compound having at least one thiol-reactive electrophilic functional group.

Any of the anti-adhesion compounds described above that possess at least one thiol-reactive electrophilic group can be used in this aspect. The term "thiol-reactive electrophilic group" as used herein is any group that is susceptible to nucleophilic attack by the lone-pair electrons on the sulfur atom of the thiol group or by the thiolate anion. Examples of thiol-reactive electrophilic groups include groups that have good leaving groups. For example, an alkyl group having a halide or alkoxy group attached to it or an α-halocarbonyl group are examples of thiol-reactive electrophilic groups. In another aspect, the thiol-reactive electrophilic group is an electron-deficient vinyl group. The term "an electron-deficient vinyl group" as used herein is a group having a carbon-carbon double bond and an electron-withdrawing group attached to one of the carbon atoms. An electron-deficient vinyl group is depicted in the formula $C_\beta=C_\alpha X$, where X is the electron-withdrawing group. When the electron-withdrawing group is attached to Cα, the other carbon atom of the vinyl group (Cβ) is more susceptible to nucleophilic attack by the thiol group. This type of addition to an activated carbon-carbon double bond is referred to as a Michael addition. Examples of electron-withdrawing groups include, but are not limited to, a nitro group, a cyano group, an ester group, an aldehyde group, a keto group, a sulfone group, or an amide group. In one aspect, the anti-adhesion compound has an electron-deficient vinyl group, wherein the electron-deficient vinyl group is an acrylate group, a methacrylate, an acrylamide, or a methacrylamide.

Figure 2:
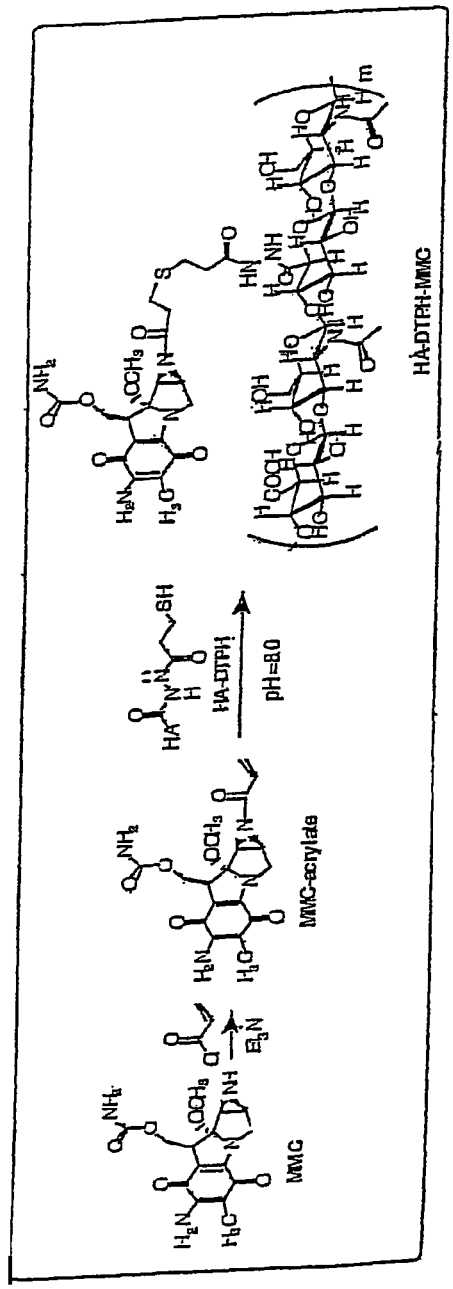
FIG. 2 shows the synthesis of HA-DTPH-MMC.

In one aspect, the anti-adhesion compound can be mitomycin C having an acrylate group. FIG. 2 depicts this aspect, where mitomycin C (MMC) can be converted to the corresponding acrylate (MMC-acrylate). In another aspect, MMC-acrylate can be then coupled with the hydrazide-modified hyaluronan thiol compound HA-DTPH (Formula III, where Y is a residue of hyaluronan and L is $CH_2CH_2CH_2$) to produce HA-DTPH-MMC (FIG. 2).

In another aspect, the first compound is produced by reacting the anti-adhesion support having at least one thiol-reactive electrophilic functional group with at least one anti-adhesion compound having at least two thiol groups. In one aspect, the anti-adhesion support having at least one thiol-reactive electrophilic functional group has the formula I

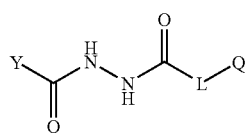

I wherein

Y can be a residue of the anti-adhesion support;

Q can be a thiol-reactive electrophilic functional group; and

L can be a polyalkylene group, a polyether group, a polyamide group, a polyimino group, a polyester, an aryl group, or a polythioether group.

In one aspect, when Q is thiol-reactive electrophilic functional group, Y can be carboxymethylcellulose, hyaluronan, or a chemically modified-derivative of hyaluronan, and L can be $CH_2CH_2$ or $CH_2CH_2CH_2$. In another aspect, Q can be an acrylate, a methacrylate, an acrylamide, or a methacrylamide adduct.

The compounds produced by coupling the anti-adhesion support with an anti-adhesion compound having at least one thiol-reactive electrophilic functional group possess at least one fragment of the formula VII

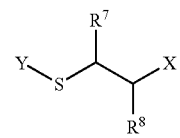

VII wherein $R^7$ and $R^9$ can be, independently, hydrogen or lower alkyl;

X can be an electron-withdrawing group attached to the anti-adhesion compound; and Y can be a residue of the anti-adhesion support.

In this aspect, X in formula VII can be any of the anti-adhesion compounds described above and Y can be a residue of any of the anti-adhesion supports described above. In one aspect, $R^7$ is hydrogen. In another aspect, $R^7$ is hydrogen; $R^8$ is hydrogen or methyl; X is a residue of mitomycin C having an electron-deficient vinyl group, and Y is a residue of carboxymethylcellulose, hyaluronan, or a chemically modified-derivative of hyaluronan.

In one aspect, the reaction between the thiol reactive compound (anti-adhesion compound or the anti-adhesion support) and the thiol compound (anti-adhesion compound or the anti-adhesion support) is generally conducted at a pH of from 7 to 12, 7.5 to 11, 7.5 to 10, or 7.5 to 9.5, or a pH of 8. In one aspect, the solvent used can be water (alone) or an aqueous solution containing an organic solvent. In one aspect, when the mixed solvent system is used, a base such as a primary, secondary, or tertiary amine can be used. In one aspect, an excess of thiol compound is used relative to the thiol-reactive compound in order to ensure that all of the thiol-reactive compound is consumed during the reaction. Depending upon the selection of the thiol reactive compound, the thiol compound, the pH of the reaction, and the solvent selected, coupling can occur from within minutes to several days. If the reaction is performed in the presence of an oxidant, such as air, the thiol compound can react with itself or another thiol compound via oxidative addition to form a disulfide linkage in addition to reacting with the thiol-reactive compound.

In another aspect, the first compound can be produced by reacting the first adhesion compound and the first adhesion support in the presence of a crosslinker.

The first adhesion compound, first adhesion support, and crosslinker can be reacted with one another in any given order. In one aspect, the crosslinker can be a thiol-reactive compound having two electron-deficient vinyl groups, wherein the two electron-deficient vinyl groups are the same. In another aspect, the thiol-reactive compound can be a diacrylate, a dimethacrylate, a diacrylamide, a dimethacrylamide, or a combination thereof.

In one aspect, the crosslinker has the formula V

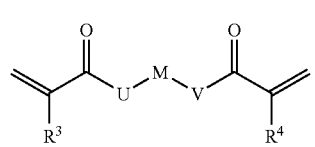

V wherein $R^3$ and $R^4$ can be, independently, hydrogen or lower alkyl;

U and V can be, independently, O or $NR^5$, wherein $R^5$ can be hydrogen or lower alkyl; and M can be a polyalkylene group, a polyether group, a polyamide group, a polyimino group, a polyester, an aryl group, or a polythioether group.

In one aspect, $R^3$ and $R^4$ are hydrogen, U and V are oxygen, and M is a polyether group. In another aspect, $R^3$ and $R^4$ are hydrogen, U and V are NH, and M is a polyether group. In a further aspect, $R^3$ and $R^4$ are methyl, U and V are oxygen, and M is a polyether group. In another aspect, $R^3$ and $R^4$ are methyl, U and V are NH, and M is a polyether group.

Figure 3:
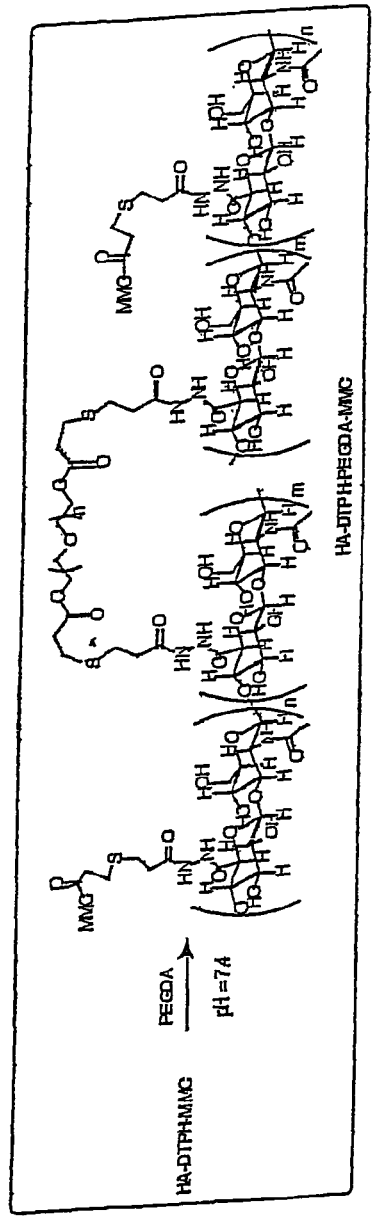
FIG. 3 shows the synthesis of HA-DTPH-PEGDA-MMC.

FIG. 3 depicts one aspect of crosslinking. HA-DTPH-MMC contains one or more free thiols groups, which then can couple with PEGDA to produce HA-DTPH-PEGDA-MMC.

The composite can optionally contain unreacted (i.e., free) anti-adhesion compound. The unreacted anti-adhesion compound can be the same or different anti-adhesion compound that is covalently bonded to the anti-adhesion support.

The composite is composed of a prohealing compound. The term "prohealing drug" as defined herein is any compound that promotes cell growth, cell proliferation, cell migration, cell motility, cell adhesion, or cell differentiation. In one aspect, the prohealing compound includes a protein or synthetic polymer. Proteins useful in the methods described herein include, but are not limited to, an extracellular matrix protein, a chemically-modified extracellular matrix protein, or a partially hydrolyzed derivative of an extracellular matrix protein. The proteins may be naturally occurring or recombinant polypeptides possessing a cell interactive domain. The protein can also be mixtures of proteins, where one or more of the proteins are modified. Specific examples of proteins include, but are not limited to, collagen, elastin, decorin, laminin, or fibronectin.

In one aspect, the synthetic polymer has at least one carboxylic acid group or the salt or ester thereof, which is capable of reacting with a hydrazide. In one aspect, the synthetic polymer comprises glucuronic acid, polyacrylic acid, polyaspartic acid, polytartaric acid, polyglutamic acid, or polyfimaric acid.

In another aspect, the prohealing compound can be any of the supports disclosed in U.S. Pat. No. 6,548,081 B2, which is incorporated by reference in its entirety. In one aspect, the prohealing compound includes cross-linked alginates, gelatin, collagen, cross-linked collagen, collagen derivatives, such as, succinylated collagen or methylated collagen, cross-linked hyaluronan, chitosan, chitosan derivatives, such as, methylpyrrolidone-chitosan, cellulose and cellulose derivatives such as cellulose acetate or carboxymethyl cellulose, dextran derivatives such carboxymethyl dextran, starch and derivatives of starch such as hydroxyethyl starch, other glycosaminoglycans and their derivatives, other polyanionic polysaccharides or their derivatives, polylactic acid (PLA), polyglycolic acid (PGA), a copolymer of a polylactic acid and a polyglycolic acid (PLGA), lactides, glycolides, and other polyesters, polyoxanones and polyoxalates, copolymer of poly(bis(p-carboxyphenoxy)propane)anhydride (PCPP) and sebacic acid, poly(1-glutamic acid), poly(d-glutamic acid), polyacrylic acid, poly(dl-glutamic acid), poly(1-aspartic acid), poly(d-aspartic acid), poly(dl-aspartic acid), polyethylene glycol, copolymers of the above listed polyamino acids with polyethylene glycol, polypeptides, such as, collagen-like, silk-like, and silk-elastin-like proteins, polycaprolactone, poly(alkylene succinates), poly(hydroxy butyrate) (PHB), poly(butylene diglycolate), nylon-2/nylon-6-copolyamides, polydihydropyrans, polyphosphazenes, poly (ortho ester), poly(cyano acrylates), polyvinylpyrrolidone, polyvinylalcohol, poly casein, keratin, myosin, and fibrin. In another aspect, cross-linked HA can be the prohealing compound.

In another aspect, the prohealing compound can be a polysaccharide. In one aspect, the polysaccharide has at least one group, such as a carboxylic acid group or the salt or ester thereof, that can react with a dihydrazide. In one aspect, the polysaccharide is a glycosaminoglycan (GAG). A GAG is one molecule with many alternating subunits. For example, HA, a non-sulfated GAG, is (GlcNAc-GlcUA-)x. Other GAGs are sulfated at different sugars. Generically, GAGs are represented by the formula A-B-A-B-A-B, where A is a uronic acid and B is an aminosugar that is either O- or N-sulfated, where the A and B units can be heterogeneous with respect to epimeric content or sulfation. Any natural or synthetic polymer containing uronic acid can be used.

There are many different types of GAGs, having commonly understood structures, which, for example, are within the disclosed compositions, such as chondroitin sulfate, dermatan, heparan, heparin, dermatan sulfate, and heparan sulfate. Any GAG known in the art can be used in any of the composites described herein. Glycosaminoglycans can be purchased from Sigma, and many other biochemical suppliers. Alginic acid, pectin, and carboxymethylcellulose are among other carboxylic acid containing polysaccharides useful in the composites described herein.

In one aspect, the prohealing compound is a compound having the formula III, where Y is a residue of a polysaccharide. In another aspect, Y is a residue of hyaluronan. HA is a non-sulfated GAG. Hyaluronan is a well known, naturally occurring, water soluble polysaccharide composed of two alternatively linked sugars, D-glucuronic acid and N-acetylglucosamine. The polymer is hydrophilic and highly viscous in aqueous solution at relatively low solute concentrations. It often occurs naturally as the sodium salt, sodium hyaluronate. Methods of preparing commercially available hyaluronan and salts thereof are well known. Hyaluronan can be purchased from Seikagaku Company, Clear Solutions Biotech, Inc., Pharmacia Inc., Sigma Inc., and many other suppliers. For high molecular weight hyaluronan it is often in the range of 100 to 10,000 disaccharide units. In another aspect, the lower limit of the molecular weight of the hyaluronan is from 10,000, 20,000, 30,000, 40,000, 50,000, 60,000, 70,000, 80,000, 90,000, or 100,000, and the upper limit is 200,000, 300,000, 400,000, 500,000, 600,000, 700,000, 800,000, 900, 000, or 1,000,000, where any of the lower limits can be combined with any of the upper limits.

The composite can optionally contain a second prohealing compound. In one aspect, the second prohealing compound can be a growth factor. Any substance or metabolic precursor which is capable of promoting growth and survival of cells and tissues or augmenting the functioning of cells is useful as a growth factor. Examples of growth factors include, but are not limited to, a nerve growth promoting substance such as a ganglioside, a nerve growth factor, and the like; a hard or soft tissue growth promoting agent such as fibronectin (FN), human growth hormone (HGH), a colony stimulating factor, bone morphogenic protein, platelet-derived growth factor (PDGF), insulin-derived growth factor (IGF-I, IGF-II), transforming growth factor-alpha (TGF-alpha), transforming growth factor-beta (TGF-beta), epidermal growth factor (EGF), fibroblast growth factor (FGF), interleukin-1 (IL-1), vascular endothelial growth factor (VEGF) and keratinocyte growth factor (KGF), dried bone material, and the like; and antineoplastic agents such as methotrexate, 5-fluorouracil, adriamycin, vinblastine, cisplatin, tumor-specific antibodies conjugated to toxins, tumor necrosis factor, and the like. The amount of growth factor incorporated into the composite will vary depending upon the growth factor and prohealing compound selected as well as the intended end-use of the composite.

Any of the growth factors disclosed in U.S. Pat. No. 6,534,591 B2, which is incorporated by reference in its entirety, can be used in this aspect. In one aspect, the growth factor includes transforming growth factors (TGFs), fibroblast growth factors (FGFs), platelet derived growth factors (PDGFs), epidermal growth factors (EGFs), connective tissue activated peptides (CTAPs), osteogenic factors, and biologically active analogs, fragments, and derivatives of such growth factors. Members of the transforming growth factor (TGF) supergene family, which are multifunctional regulatory proteins. Members of the TGF supergene family include the beta transforming growth factors (for example, TGF-β1; TGF-β2, TGF-β3); bone morphogenetic proteins (for example, BMP-1, BMP-2, BMP-3, BMP-4, BMP-5, BMP-6, BMP-7, BMP-8, BMP-9); heparin-binding growth factors (for example, fibroblast growth factor (FGF), epidermal growth factor (EGF), platelet-derived growth factor (PDGF), insulin-like growth factor (IGF)); inhibins (for example, Inhibin A, Inhibin B); growth differentiating factors (for example, GDF-1); and Activins (for example, Activin A, Activin B, Activin AB).

Growth factors can be isolated from native or natural sources, such as from mammalian cells, or can be prepared synthetically, such as by recombinant DNA techniques or by various chemical processes. In addition, analogs, fragments, or derivatives of these factors can be used, provided that they exhibit at least some of the biological activity of the native molecule. For example, analogs can be prepared by expression of genes altered by site-specific mutagenesis or other genetic engineering techniques.

In another aspect, the addition of a crogslinker can be used to couple the first compound with the prohealing compound. Any of the crosslinkers described above can be used in this aspect. In one aspect, when the first compound and the prohealing compound possess free thiol groups, a crosslinker having at least two thiol-reactive electrophilic groups can be used to couple the two compounds. Additionally, the crosslinker can couple two first compounds or two prohealing compounds.

In one aspect, the crosslinker can be a thiol-reactive compound having two electron-deficient vinyl groups, wherein the two electron-deficient vinyl groups are the same. In another aspect, the thiol-reactive compound can be a diacrylate, a dimethacrylate, a diacrylamide, a dimethacrylamide, or a combination thereof.

In another aspect, the thiol-reactive compound has the formula V

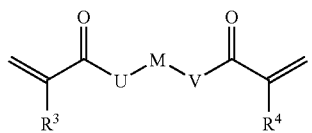

V wherein
$R^3$ and $R^4$ can be, independently, hydrogen or lower alkyl;
U and V can be, independently, O or $NR^5$, wherein $R^5$ can be hydrogen or lower alkyl; and
M can be a polyalkylene group, a polyether group, a polyamide group, a polyimino group, a polyester, an aryl group, or a polythioether group.

In one aspect, $R^3$ and $R^4$ are hydrogen, U and V are oxygen, and M is a polyether group. In another aspect, $R^3$ and $R^4$ are hydrogen, U and V are NH, and M is a polyether group. In a further aspect, $R^3$ and $R^4$ are methyl, U and V are oxygen, and M is a polyether group. In another aspect, $R^3$ and $R^4$ are methyl, U and V are NH, and M is a polyether group.

The composites described herein can assume numerous shapes and forms depending upon the intended end-use. In one aspect, the composite can be a laminate, a gel, a bead, a sponge, a film, a mesh, or a matrix. The procedures disclosed in U.S. Pat. Nos. 6,534,591 B2 and 6,548,081 B2, which are incorporated by reference in their entireties, can be used for preparing composites having different forms.

In one aspect, the composite is a laminate. In one aspect, the laminate includes a first layer and a second layer, wherein (1) the first layer comprises a first compound comprising a first anti-adhesion compound covalently bonded to a first anti-adhesion support, wherein the first layer has a first surface and a second surface, and (2) the second layer comprises a first prohealing compound, wherein the second layer has a first surface and a second surface, wherein the first surface of the first layer is adjacent to the first surface of the second layer. In this aspect, the first layer is adjacent to the second layer. Depending upon the selection of the first compound and the prohealing compound, the first compound and the prohealing compound can either be covalently bonded to one another or merely in physical contact with one another without any chemical reaction occurring between the two compounds. In one aspect, the first compound and the prohealing compound possess free thiol groups, which can form new disulfide bonds in the presence of an oxidant.

Figure 4:
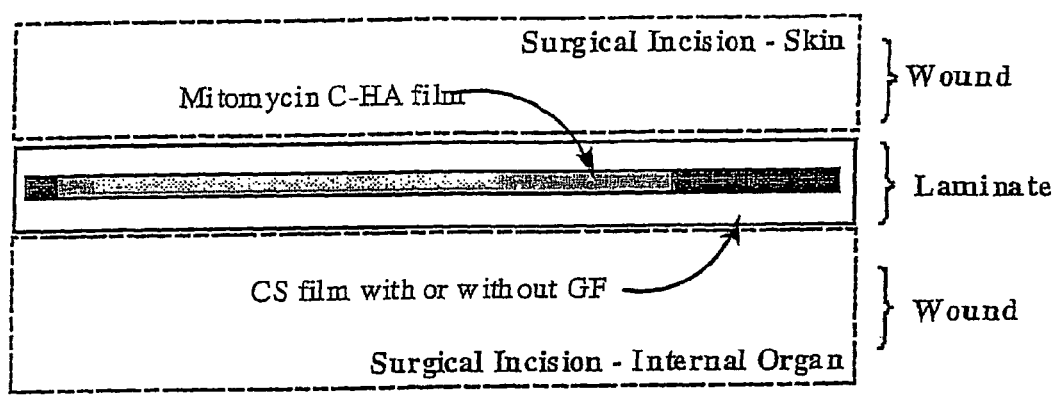
FIG. 4 shows a laminate described herein

In one aspect, a second layer of prohealing compound can be applied to a film of first layer. In one aspect, the width of the interface between the first and second layers can vary depending upon the casting time of the first layer. For example, if the casting time of the first layer is long, the width of the interface formed upon the application of the second layer will be decreased. Similarly, if the casting time of the first layer is short, a wider interface will be produced. By varying the width of the interface between the first and second layer, it is possible to create a gradient that will prevent cell growth either immediately (narrow interface) or gradually (wide interface). In another aspect, another layer of prohealing compound can be applied to the other surface of the first layer to produce a sandwich of first layer encased by prohealing compound. FIG. 4 depicts one aspect of this sandwich laminate.

In one aspect, the composite can be molded into any desired shape prior to delivery to a subject. In another aspect, the second layer (prohealing compound) can be applied to a subject followed by the application of the first compound to the exposed second layer. In a further aspect, another layer containing the prohealing compound can be applied to the exposed surface of the first layer. In this aspect, a sandwich laminate is formed in situ in the subject.

In one aspect, the first compound and prohealing compound can be used as a kit. For example, the first compound and prohealing compound are in separate syringes, with the contents being mixed using syringe-to-syringe techniques just prior to delivery to the subject. In this aspect, the first compound and prohealing compound can be extruded from the opening of the syringe by an extrusion device followed by spreading the mixture using techniques known in the art such as, for example, via spatula. In another aspect, the first compound and prohealing compound can be spread by natural means upon application to the particular area or region of interest.

In another aspect, the first compound and the prohealing compound are in separate chambers of a spray can or bottle with a nozzle or other spraying device. In this aspect, the first compound and prohealing compound do not actually mix until they are expelled together from the nozzle of the spraying device.

II. Pharmaceutical Compositions

In one aspect, any of the composites described above can include at least one pharmaceutically-acceptable compound. The resulting pharmaceutical composition can provide a system for sustained, continuous delivery of drugs and other biologically-active agents to tissues adjacent to or distant from the application site. The biologically-active agent is capable of providing a local or systemic biological, physiological or therapeutic effect in the biological system to which it is applied. For example, the agent can act to control infection or inflammation, enhance cell growth and tissue regeneration, control tumor growth, act as an analgesic, promote anti-cell attachment, and enhance bone growth, among other functions. Additionally, any of the anti-adhesion composites described herein can contain combinations of two or more pharmaceutically-acceptable compounds. In one aspect, when the composite is a laminate, the pharmaceutically-acceptable compound can be incorporated into the first and/or second layer.

In one aspect, the pharmaceutically-acceptable compounds can include substances capable of preventing an infection systemically in the biological system or locally at the defect site, as for example, anti-inflammatory agents such as, but not limited to, pilocarpine, hydrocortisone, prednisolone, cortisone, diclofenac sodium, indomethacin, $6\alpha$-methyl-prednisolone, corticosterone, dexamethasone, prednisone, and the like; antibacterial agents including, but not limited to, penicillin, cephalosporins, bacitracin, tetracycline, doxycycline, gentamycin, chloroquine, vidarabine, and the like; analgesic agents including, but not limited to, salicylic acid, acetaminophen, ibuprofen, naproxen, piroxicam, flurbiprofen, morphine, and the like; local anesthetics including, but not limited to, cocaine, lidocaine, benzocaine, and the like; immunogens (vaccines) for stimulating antibodies against hepatitis, influenza, measles, rubella, tetanus, polio, rabies, and the like; peptides including, but not limited to, leuprolide acetate (an LH-RH agonist), nafarelin, and the like. All compounds are available from Sigma Chemical Co. (Milwaukee, Wis.).

Other useful substances include hormones such as progesterone, testosterone, and follicle stimulating hormone (FSH) (birth control, fertility-enhancement), insulin, and the like; antihistamines such as diphenhydramine, and the like; cardiovascular agents such as papaverine, streptokinase and the like; anti-ulcer agents such as isopropamide iodide, and the like; bronchodilators such as metaprotemal sulfate, aminophylline, and the like; vasodilators such as theophylline, niacin, minoxidil, and the like; central nervous system agents such as tranquilizer, B-adrenergic blocking agent, dopamine, and the like; antipsychotic agents such as risperidone, narcotic antagonists such as naltrexone, naloxone, buprenorphine; and other like substances. All compounds are available from Sigma Chemical Co. (Milwaukee, Wis.).

The pharmaceutical compositions can be prepared using techniques known in the art. In one aspect, the composition is prepared by admixing the first compound and/or prohealing compound described herein with a pharmaceutically-acceptable compound prior to composite formation. The term "admixing" is defined as mixing the two components together so that there is no chemical reaction or physical interaction. The term "admixing" also includes the chemical reaction or physical interaction between the first compound or prohealing compound and the pharmaceutically-acceptable compound. Covalent bonding to reactive therapeutic drugs, e.g., those having reactive carboxyl groups, can be undertaken on the compound. For example, first, carboxylate-containing chemicals such as anti-inflammatory drugs ibuprofen or hydrocortisone-hemisuccinate can be converted to the corresponding N-hydroxysuccinimide (NHS) active esters and can further react with the $NH_2$ group of the dihydrazide-modified ant-adhesion support. Second, non-covalent entrapment of a pharmacologically active agent in the first compound and/or the prohealing compound is also possible. Third, electrostatic or hydrophobic interactions can facilitate retention of a pharmaceutically-acceptable compound in the first compound and/or the prohealing compound. For example, the hydrazido group can non-covalently interact, e.g., with carboxylic acid-containing steroids and their analogs, and anti-inflammatory drugs such as Ibuprofen (2-(4 iso-butylphenyl) propionic acid). The protonated hydrazido group can form salts with a wide variety of anionic materials such as proteins, heparin or dermatan sulfates, oligonucleotides, phosphate esters, and the like. Alternatively, the composite can be admixed with one or more pharmaceutically-acceptable compounds.

It will be appreciated that the actual preferred amounts of active pharmaceutically-acceptable compound in a specified case will vary according to the specific compound being utilized, the particular compositions formulated, the mode of application, and the particular situs and subject being treated. Dosages for a given host can be determined using conventional considerations, e.g. by customary comparison of the differential activities of the subject compounds and of a known agent, e.g., by means of an appropriate conventional pharmacological protocol. Physicians and formulators, skilled in the art of determining doses of pharmaceutical compounds, will have no problems determining dose according to standard recommendations (Physicians Desk Reference, Barnhart Publishing (1999).

Pharmaceutical compositions described herein can be formulated in any excipient the biological system or entity can tolerate. Examples of such excipients include, but are not limited to, water, saline, Ringer's solution, dextrose solution, Hank's solution, and other aqueous physiologically balanced salt solutions. Nonaqueous vehicles, such as fixed oils, vegetable oils such as olive oil and sesame oil, triglycerides, propylene glycol, polyethylene glycol, and injectable organic esters such as ethyl oleate can also be used. Other useful formulations include suspensions containing viscosity enhancing agents, such as sodium carboxymethylcellulose, sorbitol, or dextran. Excipients can also contain minor amounts of additives, such as 0.15 substances that enhance isotonicity and chemical stability. Examples of buffers include phosphate buffer, bicarbonate buffer and Tris buffer, while examples of preservatives include thimerosol, cresols, formalin and benzyl alcohol.

Pharmaceutical carriers are known to those skilled in the art. These most typically would be standard carriers for administration to humans, including solutions such as sterile water, saline, and buffered solutions at physiological pH.

Molecules intended for pharmaceutical delivery can be formulated in a pharmaceutical composition. Pharmaceutical compositions can include carriers, thickeners, diluents, buffers, preservatives, surface active agents and the like in addition to the molecule of choice. Pharmaceutical compositions can also include one or more active ingredients such as antimicrobial agents, antiinflammatory agents, anesthetics, and the like.

The pharmaceutical composition can be administered in a number of ways depending on whether local or systemic treatment is desired, and on the area to be treated. Administration can be topically (including ophthalmically, vaginally, rectally, intranasally).

Preparations for administration include sterile aqueous or non-aqueous solutions, suspensions, and emulsions. Examples of non-aqueous carriers include water, alcoholic/aqueous solutions, emulsions or suspensions, including saline and buffered media. Parenteral vehicles, if needed for collateral use of the disclosed compositions and methods, include sodium chloride solution, Ringer's dextrose, dextrose and sodium chloride, lactated Ringer's, or fixed oils. Intravenous vehicles, if needed for collateral use of the disclosed compositions and methods, include fluid and nutrient replenishers, electrolyte replenishers (such as those based on Ringer's dextrose), and the like. Preservatives and other additives can also be present such as, for example, antimicrobials, anti-oxidants, chelating agents, and inert gases and the like.

Formulations for topical administration can include ointments, lotions, creams, gels, drops, suppositories, sprays, liquids and powders. Conventional pharmaceutical carriers, aqueous, powder or oily bases, thickeners and the like can be necessary or desirable.

Dosing is dependent on severity and responsiveness of the condition to be treated, but will normally be one or more doses per day, with course of treatment lasting from several days to several months or until one of ordinary skill in the art determines the delivery should cease. Persons of ordinary skill can easily determine optimum dosages, dosing methodologies and repetition rates.

In one aspect, any of the composites and pharmaceutical compositions described herein can include living cells or genes. Examples of living cells include, but are not limited to, fibroblasts, hepatocytes, chondrocytes, stem cells, bone marrow, muscle cells, cardiac myocytes, neuronal cells, or pancreatic islet cells. Any of the cells and genes disclosed in U.S. Pat. No. 6,534,591 B2, which is incorporated by reference in its entirety, can be used.

III. Methods of Use

The composites and pharmaceutical compositions described herein can be used for a variety of uses related to drug delivery, small molecule delivery, wound healing, burn injury healing, and tissue regeneration. The disclosed compositions are useful for situations which benefit from a hydrated, pericellular environment in which assembly of other matrix components, presentation of growth and differentiation factors, cell migration, or tissue regeneration are desirable.

The composites and pharmaceutical compositions described herein can be placed directly in or on any biological system without purification as it is composed of biocompatible materials. Examples of sites the composites can be placed include, but not limited to, soft tissue such as muscle or fat; hard tissue such as bone or cartilage; areas of tissue regeneration; a void space such as periodontal pocket; surgical incision or other formed pocket or cavity, a natural cavity such as the oral, vaginal, rectal or nasal cavities, the cul-de-sac of the eye, and the like; the peritoneal cavity and organs contained within, and other sites into or onto which the compounds can be placed including a skin surface defect such as a cut, scrape or burn area. The anti-adhesion composites described herein can be biodegradable and naturally occurring enzymes will act to degrade them over time. Components of the anti-adhesion composites can be "bioabsorbable" in that the components of the composite will be broken down and absorbed within the biological system, for example, by a cell, tissue and the like. Additionally, the composites, especially composites that have not been rehydrated, can be applied to a biological system to absorb fluid from an area of interest.

The composites and compositions described herein can be used in a number of different surgical procedures. In one aspect, the composites and compositions can be used in any of the surgical procedures disclosed in U.S. Pat. Nos. 6,534,591 B2 and 6,548,081 B2, which are incorporated by reference in their entireties. In one aspect, the composites and compositions described herein can be used in cardiosurgery and articular surgery, abdominal surgery where it is important to prevent adhesions of the intestine or the mesentery, thoracic surgery involving the lungs and heart (e.g., heart bypass or transplant surgery); operations performed in the urogenital regions where it is important to ward off adverse effects on the ureter and bladder, and on the functioning of the oviduct and uterus; and nerve surgery operations where it is important to minimize the development of granulation tissue. In surgery involving tendons, there is generally a tendency towards adhesion between the tendon and the surrounding sheath or other surrounding tissue during the immobilization period following the operation. In another aspect, the composites and compositions described herein can be used to prevent adhesions after laparascopic surgery, pelvic surgery, oncological surgery, sinus and craniofacial surgery, ENT surgery, or in procedures involving spinal dura repair.

In another aspect, the composites and compositions can be used in opthalmological surgery. In opthalmological surgery, a biodegradable implant could be applied in the angle of the anterior chamber of the eye for the purpose of preventing the development of synechiae between the cornea and the iris; this applies especially in cases of reconstructions after severe damaging events. Moreover, degradable or permanent implants are often desirable for preventing adhesion after glaucoma surgery and strabismus surgery.

In another aspect, the composites and compositions described herein can be used for the augmentation of soft or hard tissue. In another aspect, the composites and compositions described herein can be used to coat implants. In another aspect, the composites and compositions described herein can be used to treat aneurisms.

The composites described herein can be used as a carrier and delivery device for a wide variety of releasable pharmaceutically-acceptable compounds having curative or therapeutic value for human or non-human animals. Any of the pharmaceutically-acceptable compounds described above can be used in this aspect. Many of these substances which can be carried by the anti-adhesion composites are discussed above. Depending upon the selection of the pharmaceutically-acceptable compound, the pharmaceutically-acceptable compound can be present in the first compound or the prohealing compound. Included among pharmaceutically-acceptable compounds that are suitable for incorporation into the composites described herein are therapeutic drugs, e.g., anti-inflammatory agents, anti-pyretic agents, steroidal and non-steroidal drugs for anti-inflammatory use, hormones, growth factors, contraceptive agents, antivirals, antibacterials, antifungals, analgesics, hypnotics, sedatives, tranquilizers, anti-convulsants, muscle relaxants, local anesthetics, antispasmodics, antiulcer drugs, peptidic agonists, sympathiomimetic agents, cardiovascular agents, antitumor agents, oligonucleotides and their analogues and so forth. The pharmaceutically-acceptable compound is added in pharmaceutically active amounts.

The rate of drug delivery depends on the hydrophobicity of the molecule being released. For example, hydrophobic molecules, such as dexamethazone and prednisone are released slowly from the compound as it swells in an aqueous environment, while hydrophilic molecules, such as pilocarpine, hydrocortisone, prednisolone, cortisone, diclofenac sodium, indomethacin, 6∝-methyl-prednisolone and corticosterone, are released quickly. The ability of the compound to maintain a slow, sustained release of steroidal anti-inflammatories makes the compounds described herein extremely useful for wound healing after trauma or surgical intervention.

In certain methods the delivery of molecules or reagents related to angiogenesis and vascularization are achieved. Disclosed are methods for delivering agents, such as VEGF, that stimulate microvascularization. Also disclosed are methods for the delivery of agents that can inhibit angiogenesis and vascularization, such as those compounds and reagents useful for this purpose disclosed in but not limited to U.S. Pat. No. 6,174,861 for "Methods of inhibiting angiogenesis via increasing in vivo concentrations of endostatin protein;" U.S. Pat. No. 6,086,865 for "Methods of treating angiogenesis-induced diseases and pharmaceutical compositions thereof;" U.S. Pat. No. 6,024,688 for "Angiostatin fragments and method of use;" U.S. Pat. No. 6,017,954 for "Method of treating tumors using O-substituted fumagillol derivatives;" U.S. Pat. No. 5,945,403 for "Angiostatin fragments and method of use;" U.S. Pat. No. 5,892,069 "Estrogenic compounds as anti-mitotic agents;" for U.S. Pat. No. 5,885,795 for "Methods of expressing angiostatic protein;" U.S. Pat. No. 5,861,372 for "Aggregate angiostatin and method of use;" U.S. Pat. No. 5,854,221 for "Endothelial cell proliferation inhibitor and method of use;" U.S. Pat. No. 5,854,205 for "Therapeutic antiangiogenic compositions and methods;" U.S. Pat. No. 5,837,682 for "Angiostatin fragments and method of use;" U.S. Pat. No. 5,792,845 for "Nucleotides encoding angiostatin protein and method of use;" U.S. Pat. No. 5,733,876 for "Method of inhibiting angiogenesis;" U.S. Pat. No. 5,698,586 for "Angiogenesis inhibitory agent;" U.S. Pat. No. 5,661,143 for "Estrogenic compounds as anti-mitotic agents;" U.S. Pat. No. 5,639,725 for "Angiostatin protein;" U.S. Pat. No. 5,504,074 for "Estrogenic compounds as anti-angiogenic agents;" U.S. Pat. No. 5,290,807 for "Method for regressing angiogenesis using o-substituted fumagillol derivatives;" and U.S. Pat. No. 5,135,919 for "Method and a pharmaceutical composition for the inhibition of angiogenesis" which are herein incorporated by reference for the material related to molecules for angiogenesis inhibition.

In one aspect, the pharmaceutically-acceptable compound is pilocarpine, hydrocortisone, prednisolone, cortisone, diclofenac sodium, indomethacin, 6∝-methyl-prednisolone, corticosterone, dexamethasone and prednisone. However, methods are also provided wherein delivery of a pharmaceutically-acceptable compound is for a medical purpose selected from the group of delivery of contraceptive agents, treating postsurgical adhesions, promoting skin growth, preventing scarring, dressing wounds, conducting viscosurgery, conducting viscosupplementation, engineering tissue.

In one aspect, the anti-adhesion composites and compositions described herein can be used for the delivery of living cells to a subject. Any of the living cells described above can be used in the aspect. In one aspect, the living cells are part of the prohealing compound. For example, when the composite is a laminate, the living cells are present in the prohealing layer.

In one aspect, the anti-adhesion composites and compositions can be used for the delivery of growth factors and molecules related to growth factors. Any of the growth factors described above are useful in this aspect. In one aspect, the growth factor is part of the prohealing compound.

In one aspect, described herein are methods for reducing or inhibiting adhesion of two tissues in a surgical wound in a subject by contacting the wound of the subject with any of the composites or compositions described herein. Not wishing to be bound by theory, it is believed that the first compound will prevent tissue adhesion between two different tissues (e.g., organ and skin tissue). It is desirable in certain post-surgical wounds to prevent the adhesion of tissues in order to avoid future complications. The second layer and optional third layer will promote healing of the tissues. Any of the prohealing compounds described above can be used as the second or third layer. In one aspect, the second and third layer can be chemically modified-heparin, chemically modified-hyaluronan, or a chemically-modified glycosaminoglycan such as, for example, chemically-modified chondroitin sulfate. FIG. 4 depicts one aspect of this methodology. In this aspect, the first layer is composed of mitomycin C-chemically modified-hyaluronan, which is sandwiched by a second and third layer of chemically modified-chondroitin sulfate that optionally contains a growth factor. The chemically modified-chondroitin sulfate layers are in contact with the skin and organ tissue. Here, the mitomycin C-chemically modified-hyaluronan layer prevents adhesion between the skin and organ tissues.

In another aspect, when the composite is laminate, the laminate includes a first layer of anti-adhesion compound/support and a second layer composed of a prohealing compound, wherein the laminate is wrapped around a tissue. For example, the laminate can be wrapped around a tendon, where the first layer is in contact with the tendon, and the second layer is in contact with surrounding muscle tissue. In this aspect, the laminate contributes a cylindrical anti-adhesion layer around the tendon, while healing of the tendon is promoted by the inner layer of the cylindrical material.

The composites described herein provide numerous advantages. For example, the composites provide a post-operative adhesion barrier that is at least substantially resorbable and, therefore, does not have to be removed surgically at a later date. Another advantage is that the composites are also relatively easy to use, can be formulated to hold sutures, and can stay in place after it is applied.

In another aspect, described herein are methods for improving wound healing in a subject in need of such improvement by contacting any of the composites or pharmaceutical compositions described herein with a wound of a subject in need of wound healing improvement. Also provided are methods to deliver at least one pharmaceutically-acceptable compound to a patient in need of such delivery by contacting any of the anti-adhesion composites or pharmaceutical compositions described herein with at least one tissue capable of receiving said pharmaceutically-acceptable compound.

The disclosed composites and compositions can be used for treating a wide variety of tissue defects in an animal, for example, a tissue with a void such as a periodontal pocket, a shallow or deep cutaneous wound, a surgical incision, a bone or cartilage defect, and the like. For example, the composites described herein can be in the form of a hydrogel film. The hydrogel film can be applied to a defect in bone tissue such as a fracture in an arm or leg bone, a defect in a tooth, a cartilage defect in the joint, ear, nose, or throat, and the like. The hydrogel film composed of the composites described herein can also function as a barrier system for guided tissue regeneration by providing a surface on or through which the cells can grow. To enhance regeneration of a hard tissue such as bone tissue, it is preferred that the hydrogel film provides support for new cell growth that will replace the matrix as it becomes gradually absorbed or eroded by body fluids.

The anti-adhesion composites described herein can be delivered onto cells, tissues, and/or organs, for example, by injection, spraying, squirting, brushing, painting, coating, and the like. Delivery can also be via a cannula, catheter, syringe with or without a needle, pressure applicator, pump, and the like. The composite can be applied onto a tissue in the form of a film, for example, to provide a film dressing on the surface of the tissue, and/or to adhere to a tissue to another tissue or hydrogel film, among other applications.

In one aspect, the anti-adhesion composites described herein are administered via injection. For many clinical uses, when the composite is in the form of a hydrogel film, injectable hydrogels are preferred for three main reasons. First, an injectable hydrogel could be formed into any desired shape at the site of injury. Because the initial hydrogels can be sols or moldable putties, the systems can be positioned in complex shapes and then subsequently crosslinked to conform to the required dimensions. Second, the hydrogel would adhere to the tissue during gel formation, and the resulting mechanical interlocking arising from surface microroughness would strengthen the tissue-hydrogel interface. Third, introduction of an in situ-crosslinkable hydrogel could be accomplished using needle or by laparoscopic methods, thereby minimizing the invasiveness of the surgical technique.

The anti-adhesion composites described herein can be used to treat periodontal disease, gingival tissue overlying the root of the tooth can be excised to form an envelope or pocket, and the composition delivered into the pocket and against the exposed root. The composites can also be delivered to a tooth defect by making an incision through the gingival tissue to expose the root, and then applying the material through the incision onto the root surface by placing, brushing, squirting, or other means.

When used to treat a defect on skin or other tissue, the anti-adhesion composites described herein can be in the form of a hydrogel film that can be placed on top of the desired area. In this aspect, the hydrogel film is malleable and can be manipulated to conform to the contours of the tissue defect.

The anti-adhesion composites described herein can be applied to an implantable device such as a suture, claps, prosthesis, catheter, metal screw, bone plate, pin, a bandage such as gauze, and the like, to enhance the compatibility and/or performance or function of an implantable device with a body tissue in an implant site. The composites can be used to coat the implantable device. For example, the composites could be used to coat the rough surface of an implantable device to enhance the compatibility of the device by providing a biocompatible smooth surface which reduces the occurrence of abrasions from the contact of rough edges with the adjacent tissue. The composites can also be used to enhance the performance or function of an implantable device. For example, when the composite is a hydrogel film, the hydrogel film can be applied to a gauze bandage to enhance its compatibility or adhesion with the tissue to which it is applied. The hydrogel film can also be applied around a device such as a catheter or colostomy that is inserted through an incision into the body to help secure the catheter/colosotomy in place and/or to fill the void between the device and tissue and form a tight seal to reduce bacterial infection and loss of body fluid.

It is understood that the disclosed composites and compositions can be applied to a subject in need of tissue regeneration. For example, cells can be incorporated into the composites described herein for implantation. Examples of subjects that can be treated with the composites described herein include mammals such as mice, rats, cows or cattle, horses, sheep, goats, cats, dogs, and primates, including apes, chimpanzees, orangatangs, and humans. In another aspect, the composites and compositions described herein can be applied to birds.

When being used in areas related to tissue regeneration such as wound or burn healing, it is not necessary that the disclosed composites, compositions, and methods eliminate the need for one or more related accepted therapies. It is understood that any decrease in the length of time for recovery or increase in the quality of the recovery obtained by the recipient of the disclosed composites, compositions, and methods has obtained some benefit. It is also understood that some of the disclosed composites, compositions, and methods can be used to prevent or reduce fibrotic adhesions occurring as a result of wound closure as a result of trauma, such surgery. It is also understood that collateral affects provided by the disclosed composites, compositions, and methods are desirable but not required, such as improved bacterial resistance or reduced pain etc.

It is understood that any given particular aspect of the disclosed composites, compositions and methods can be easily compared to the specific examples and embodiments disclosed herein, including the non-polysaccharide based reagents discussed in the Examples. By performing such a comparison, the relative efficacy of each particular embodiment can be easily determined. Particularly preferred assays for the various uses are those assays which are disclosed in the Examples herein, and it is understood that these assays, while not necessarily limiting, can be performed with any of the composites, compositions, and methods disclosed herein.

EXAMPLES

The following examples are put forth so as to provide those of ordinary skill in the art with a complete disclosure and description of how the compounds, compositions, and methods described and claimed herein are made and evaluated, and are intended to be purely exemplary and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, desired solvents, solvent mixtures, temperatures, pressures and other reaction ranges and conditions that can be used to optimize the product purity and yield obtained from the described process. Only reasonable and routine experimentation will be required to optimize such process conditions.

I. Materials

Fermentation-derived hyaluronan (HA, sodium salt, Mw=1.5 MDa) was purchased from Clear Solutions Biotech, Inc. (Stony Brook, N.Y.). 1-Ethyl-3-[3-(dimethylamino) propyl]carbodiimide (FDCI), triethylamine (IEA), 3,3'-dithiobis (propanoic acid), acryloyl chloride and hydrazine hydrate were from Aldrich Chemical Co. (Milwaukee, Wis.). Dulbecco's phosphate-buffered saline (DPBS) and propidium iodide (PI) were from Sigma Chemical Co. (St. Louis, Mo.). Dithiothreitol (DTT) was from Diagnostic Chemicals Limited (Oxford, Conn.). 5,5'-Dithiobis(2-nitrobenzoic acid) (DTNB) was from Acros (Houston, Tex.). MMC was from ICN Biomedicals Inc. (Aurora, Ohio). PEGDA ($M_w$ 3400 Da) was from Shearwater Polymers (Huntsville, Ala.). Fluorescein diacetate (F-DA) was from Molecular Probes (Eugene, Oreg.). $^1$H and $^{13}$C NMR were obtained using a Varian INOVA 400 at 400 MHz and 100 MHz respectively in the solvent indicated. UV-vis spectral data were obtained using a Hewlett-Packard 8453 UV-visible spectrophotometer (Palo Alto, Calif.). Thiolated HA (42% modification, i.e., 42 thiol groups per 100 disaccharide units, $M_w$ 158 kDa, $M_n$ 78 kDa, polydispersity index=2.03) was synthesized as described (Shu, X. Z.; Liu, Y.; Luo, Y.; Roberts, M. C.; Prestwich, G. D. *Biomacromolecules* 2002, 3, 1304-1311), which is incorporated by reference in its entirety.

II. Synthesis of Hydrogels a. Synthesis of MMC-Acrylate

Mitomycin C (2 mg) was dissolved in 10 ml dried methylene chloride, and 1.7 μl TEA and 1 μl distilled acryloyl chloride were added subsequently. The reaction mixture was stirred at room temperature for 4 hours, then concentrated and purified by a silica column (methylene chloride:methanol=20:1). The yield is 1.78 mg. $^1$H NMR (400 MHz, MeOD-$d_3$): δ 6.31 (dd, J=2, J=10, 2'-H), 1.82 (dd, J=10, J=2.4, 1H, 3'-H), 5.48 (d, J=0.8, 1H, 3'-H), 4.81 (dd, obscured by MeOH, 1H, 10-H), 4.49 (d, J=13, 1H, 3-H), 3.93 (t, J=11, 1H, 3-H), 3.67 (d, J=4.4, 1H, 10-H), 3.64 (d, J=4.8, 1H, 9-H), 3.51 (d, J=12, 1H, 1-H), 3.48 (dd, J=1.2, J=4.8, 1H, 2-H), 3.24 (s, 3H, 9α-OCH$_3$), 1.75 (s, 3H, 6-CH$_3$). $^{13}$C NMR (400 Mz, MeOD-d3): δ177.7 (C-1'), 176.1 (C-5), 176.0 (C-8), 158.4 (CONH$_2$), 155.4 (C-4a), 149.7 (C-7), 130.4 (C-2'), 129.4 (C-3'), 109.9 (C-8a), 106.0 (C-9a), 103.8 (C-6), 61.5 (C-10), 53.6 (C-9), 49.0 (9a-OCH$_3$), 48.9 (C-3), 42.3 (C-1), 40.9 (C-2), 6.9 (6-CH$_3$).

b. Preparation of MMC-HA

Model Reaction of MMC-Acrylate with Thiol Group:

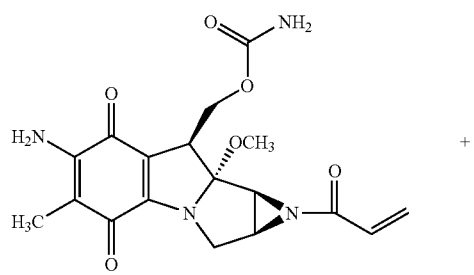

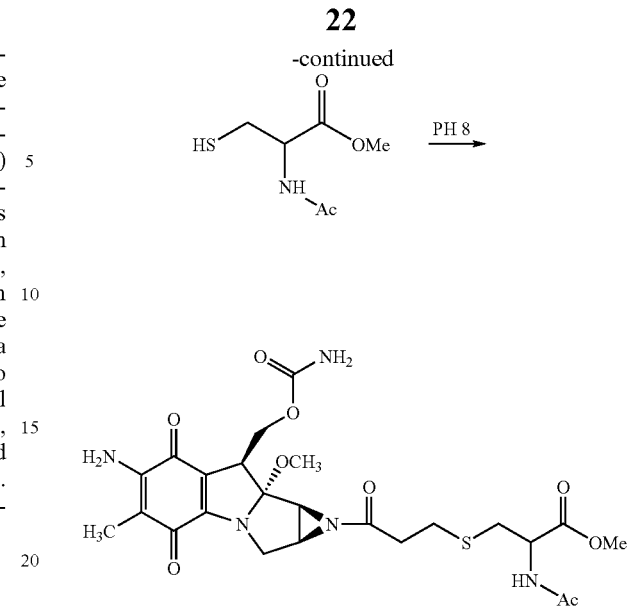

The reaction time of MMC-acrylate conjugate to thiolated HA was determined by a model reaction. N-acetyl cysteine methyl ester was used as a model reagent to react with MMC-acryloyl. The concentration of thiol group was measured using 2-nitro-5-thiosulfobenzoate (NTSB) or Ellman reagent. The reaction was performed in PBS buffer (pH 8.0) with a concentration of MMC-acrylate of 0.3 mg/mL and an initial ratio of 2 acrylates to 1 thiol. To a 0.3 mg/mL solution of MMC-acrylamide in DPBS buffer (pH 8.0) was added 0.5 equivalents of N-acetyl cysteine methyl ester, giving a ratio of two acrylamide groups per thiol. The concentration of remaining thiols was measured using NTSB or Ellman's reagent. The conjugate addition adduct was isolated by silica chromatography (methylene chloride:methanol=20:1). $^1$H NMR (400 MHz, CD$_3$OD): δ 4.75 (dd, obscured by MeOH, 1H, H-10), 4.50 (dd, J=4.8 Hz, J=7.6 Hz, 1H, H-6'), 4.36 (d, J=13 Hz, 1H, H-3), 3.90 (t, J=10.8 Hz, 1H, H-3), 3.63 (s, 3H, 7'-OCH$_3$), 3.59 (d, J=4 Hz, 1H, H-10), 3.55 (d, J=4 Hz, 1H, H-9), 3.45 (d, J=4.4 Hz, 1H, H-1), 3.41 (d, J=2 Hz, 1H, H-2), 3.15 (s, 3H, 9a-OCH$_3$), 2.6~3.1 (m, 6H, H-2', H-3', H-5'), 1.90 (s, 3H, 1"-CH$_3$), 1.67 (s, 3H, 6-CH$_3$). $^{13}$C NMR (400 MHz, CD$_3$OD): δ 182.7 (C-5), 177.7 (C-8), 176.0 (C-1'), 172.1 (C-7'), 171.4 (C-1"), 158.4 (CONH$_2$), 155.4 (C-4a), 149.7 (C-7), 109.8 (C-8a), 105.9 (C-9a), 103.8 (C-6), 61.5 (C-10), 53.6 (C-9), 52.6 (C-6'), 51.7 (7'-OCH$_3$), 48.9 (9a-OCH$_3$), 48.9 (C-3), 42.4 (C-1), 39.9 (C-2), 36.6 (C-2'), 33.3 (C-5'), 27.0 (C-3'), 21.1 (1"-CH$_3$), 6.9 (6-CH$_3$). MS (ESI) m/z 566.2 M+1 (100).

Preparation of HA-MMC Conjugate

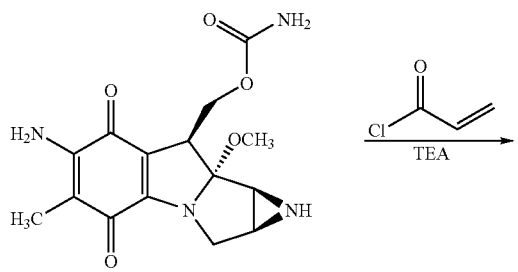

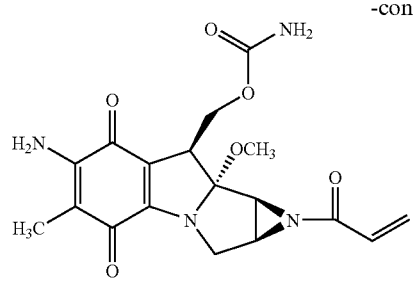
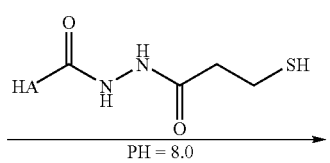

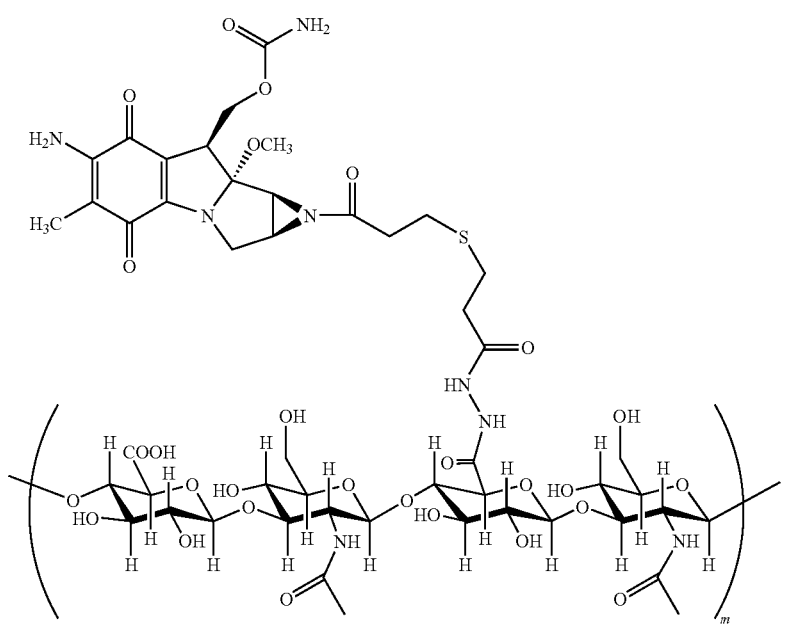

Thiolated HA was dissolved in PBS buffer to the concentration of 1.25% (w/v). Modified MMC was dissolved in minimal ethanol and added into the HA-DTPH solution. The theoretical MMC loading to the disaccharides was 0.5%, 1% and 2% respectively. The procedure was conducted under N₂ protection and the final pH of the mixture was adjusted to 8.0. The reaction was processed for three hours with stirring.

c. Preparation of HA-MMC-PEG Hydrogel Films

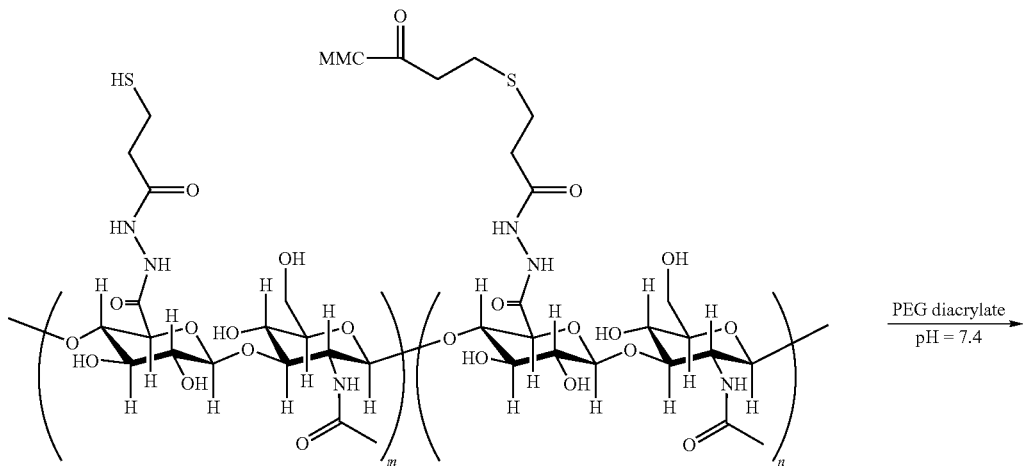

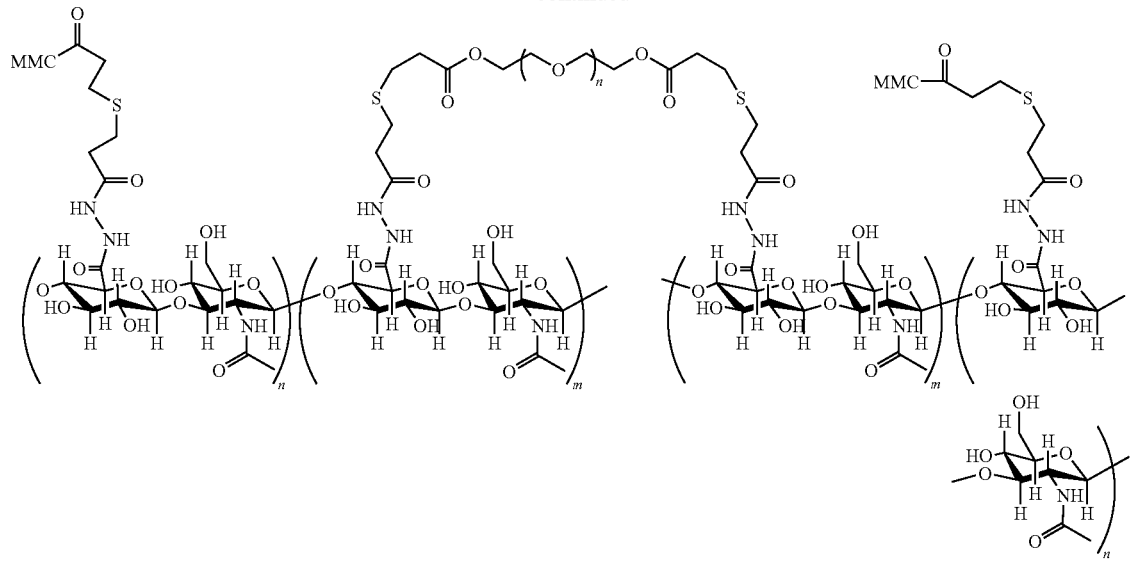

Procedure 1

HA-MMC solution was adjusted to pH 7.4 after the coupling reaction. PEG diacrylate was dissolved in PBS buffer to the concentration of 4.5% (w/v). The two solutions were mixed together and vortexed for one minute. The reaction mixture was removed by Eppendorf® Combitips and added to 2 cm×2 cm dishes, 2 mL/dishes. The hydrogels were formed in about half hour and were evaporated in air to dryness for several days to form the films.

Procedure 2

The pKa value for thiolated HA was determined to be 8.87. The thiolated HA was dissolved in DPBS buffer to a concentration of 1.25% (w/v) and the pH was adjusted to 8.0. MMC-acrylamide was dissolved in a minimal volume of ethanol and added dropwise to the stirred thiolated HA solution. The theoretical MMC loadings, 0.5% and 2%, were calculated relative to the HA disaccharide unit. All procedures were performed under a nitrogen atmosphere to minimize disulfide formation, and each reaction was stirred for 3 h. After the coupling reaction, the HA-DTPH-MMC solution was then adjusted to pH 7.4 by addition of 1 N HCl. PEGDA was dissolved in DPBS buffer to give a stock concentration of 4.5% (w/v). The 1 volume of PEGDA stock was added to four volumes of HA-DTPH-MMC solution, and the mixture was stirred and vortexed for 1 min. Aliquots (2.0 mL) of the HA-DTPH-MMC-PEGDA reaction mixture were removed with plastic Eppendorf® Combitips and added to 2 cm×2 cm dishes. The hydrogels began to gel in 10 min, and gelation was essentially complete by 30 min. Plates were then transferred to a hood and allowed to further crosslink in air; after three days, pliable hydrogel films (0.10 mm thick) had formed.

III. In Vitro Release Studies

MMC Release Experiment

Dried hydrogel films were cut into 2 cm squares. The square gel film and the cut off margin were weighed separately, and the MMC contained in each square film was calculated. Each film was dipped into 5 mL of 100 mM PBS buffer and shaken gently at 37° C. At each time point, 0.5 mL solution was removed and 0.5 mL fresh PBS buffer was added. The solution containing released MMC was detected at a wavelength of 358 μm. The accumulated concentration of released MMC was plotted as a function of the time.

Figure 5:
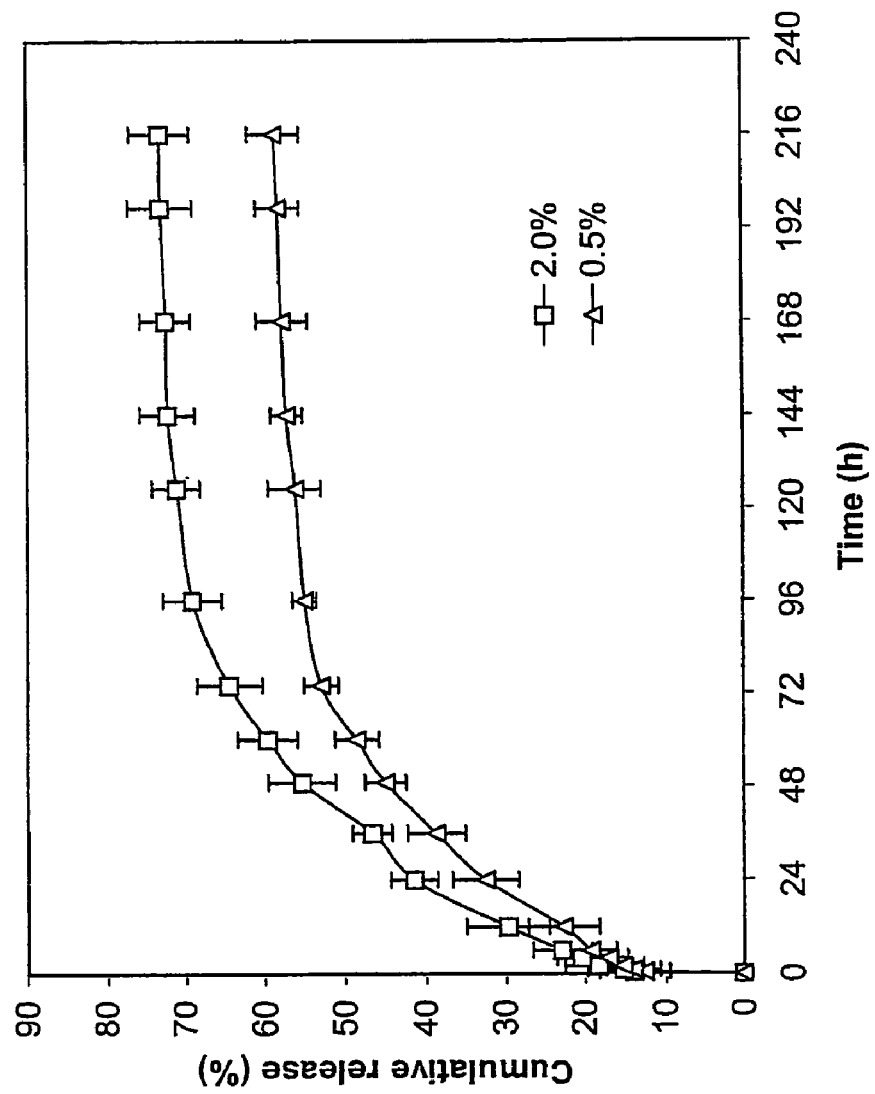
FIG. 5 show the results of in vitro MMC release.

FIGS. 5a-5c show the results of in vitro MMC release results. FIG. 5a shows the absolute released concentration. The released MMC is proportional to the MMC contained in the hydrogel. The relative release pattern is shown in FIG. 5b after replotting the data. HA films with 1% and 2% MMC loadings have similar release profiles. At the first half hour, about 13% MMC was released from the hydrogel, which may come from two sources: one was the un-coupled MMC, the other was hydrolyzed MMC. Then a slow release pattern was observed with a half-life of approximately 48 hours. The release of MMC continued for 5 days until reaching a plateau. A considerable amount of MMC remained in the film after 8 days. The release profile 0.5% MMC is depicted in FIG. 5c, where the amount of MMC released was proportional to the amount of starting amount of MMC in the hydrogel.

IV. In Vitro Cytotoxicity

Cell proliferation and cell morphology were examined in separate experiments. First, T31 human tracheal scar fibroblasts were seeded in 12-well cell culture inserts (Fisher, Marshalltown, Iowa), cultured for 24 h, and then transferred into 12-well cell culture plate that had been pre-coated with HA-DTPH-MMC-PEGDA films (1 mL gel per well). Next, 2.5 mL of a 1:1 mixture of Dulbecco's modified Eagle Medium and Nutrient Mixture F-12 (D-MEM/F-12) (GIBCO, Rockville, Md.) containing 10% newborn calf serum (NBCS) was added to each well. Four 2-mm diameter holes were made with 16 gauge needles on the side of the inserts closest to the bottom to ensure that the medium could be easily exchanged between the inserts and the wells of the plates. At day 0, 1, 3, and 5, six inserts from each group were transferred into a new 12-well plate, and 1 mL of D-MEM/F-12 medium containing 15% (v/v) of CellTiter 96 Proliferation Kit solution (MTS assay, Promega, Madison, Wis.) and 5% (v/v) of NBCS were added into each insert. The plate was incubated at 37° C. 5% $CO_2$ on a shaker for 2 h. Then, aliquots (150 μL) of the media were transferred into a 96-well plate and read at 550 nm with an OPTI Max microplate reader (Molecular Devices). The absorbance reading was converted into a cell number based on standard curves that were generated from the assay of known numbers of cells.

To monitor changes in cell morphology, T31 fibroblasts (30,000 cells) were seeded into each chamber of two-well chamber slide (Fisher) and cultured for 24 h. A plastic scaffold made from the cap of T75 cell culture flask (Fisher) was added into each chamber followed by addition of HA-DTPH-MMC-PEGDA films (5×5 mm) on the top of each scaffold. Next, 2.5 mL of D-MEM/F-12 culture medium containing 10% NBCS was added into each chamber. After three days in culture, the films and scaffolds were removed, and the cells were observed using a confocal laser scanning microscope (LSM 510, Carl Zeiss Microimaging, Inc., Thornwood, N.Y.) after being double-stained by F-DA and PI. On days 0, 1, 3, and 5, the quantity of living cells was determined by an MTS (CellTitler Proliferation) assay. The cell morphology was also studied by culturing the cells on chamber slides, without direct contact with the films, which were on the top of the specially-designed scaffolds. On day 3, the cells were observed under confocal laser scanning microscope and double-stained with F-DA and PI.

Figure 9:
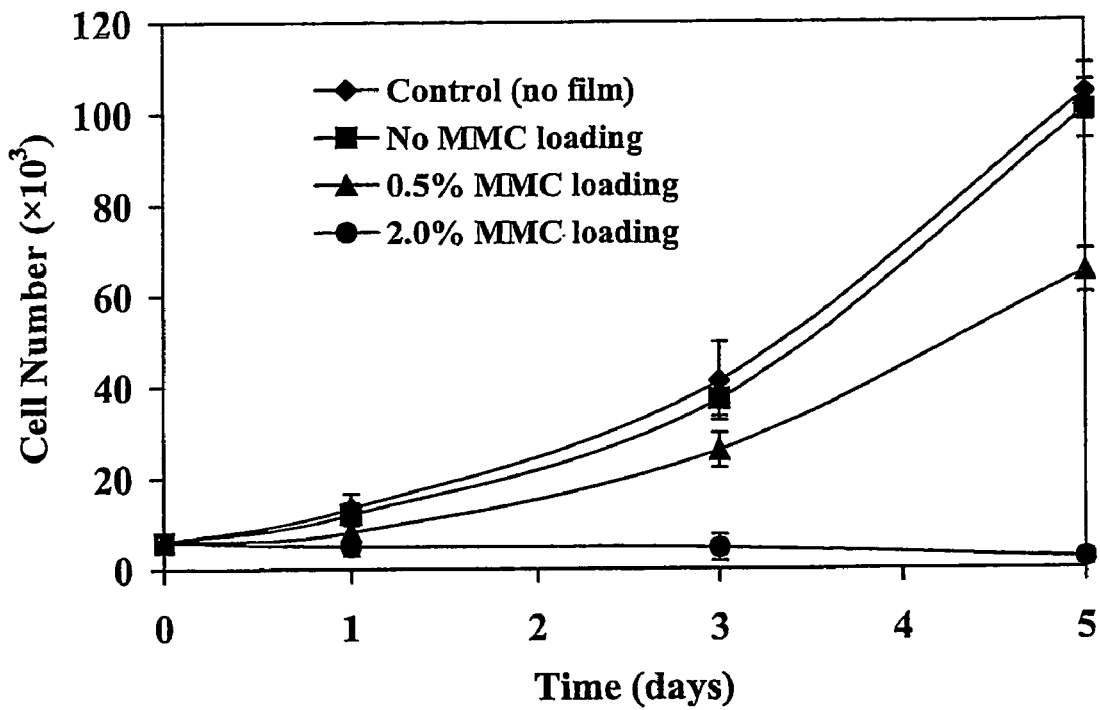
FIG. 9 shows the in vitro cell proliferation of T31 human tracheal scar fibroblasts cultured in the presence of HA-DTPH-PEGDA films with different concentrations of MMC and compared with no-film controls for up to 5 days.

As shown in FIG. 9, the cells cultured in the presence of HA-DTPH-PEGDA film (i.e., 0% MMC) proliferated as fast as the no-film control cells. In contrast, cell proliferation was significantly decreased in the presence of the HA-DTPH-MMC-PEGDA films containing 0.5% MMC. With a concentration of 2.0% MMC, cell proliferation was stopped and cells began to die. Thus, the HA-DTPH-PEGDA film lacking MMC showed no cytotoxicity and the anti-proliferative effects were entirely due to MMC released from the films.

Figure 10:
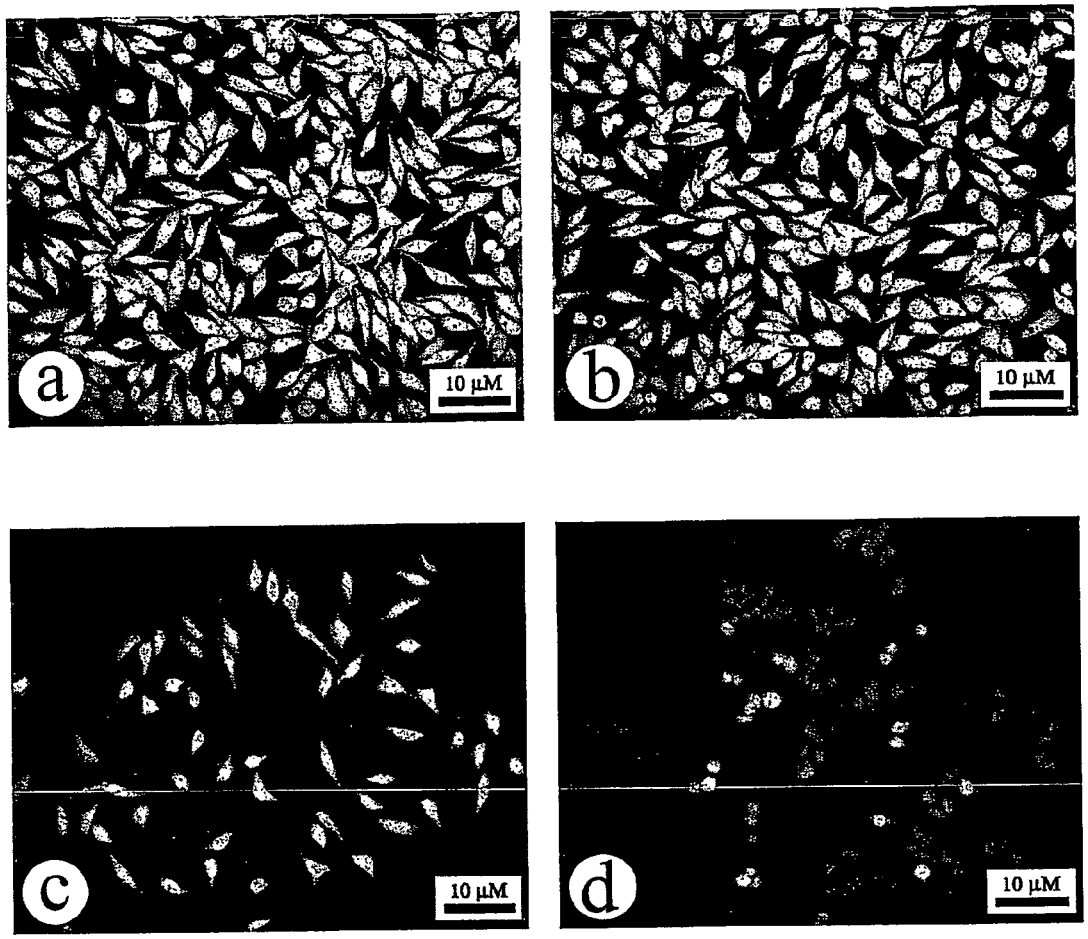
FIG. 10 shows the in vitro culture of human T31 fibroblasts in the presence of HA-DTPH-MMC-PEGDA films with different concentrations of MMC, wherein the cells were double-stained with F-DA (green, live cells) and propidium iodide (PI) (red, dead cells).

The morphology and density of the cells are illustrated in FIG. 10, in which living cells are stained green and dead cells are stained red ((a) Control, no film; (b) HA-DTPH-PEGDA films lacking MMC; (c) HA-DTPH-MMC-PEGDA films with 0.5% MMC; and (d) HA-DTPH-MMC-PEGDA films with 2.0% MMC. Scale bar: 10 μm.). The results were consistent with that obtained from MTS assay. The cell density in the presence of HA-DTPH-PEGDA film (FIG. 10b) was similar to the no-film control group (FIG. 10a). Cell growth was partially inhibited in the presence of HA-DTPH-MMC-PEGDA films with 0.5% MMC (FIG. 10c). An even larger number of dead cells were found when the cells were indirectly exposed to the HA-DTPH-MMC-PEGDA films containing 2% MMC (FIG. 10d).

In summary, the in vitro cytotoxicity experiments illustrated that MMC was released from the film, and that the released MMC maintained its anti-proliferative activity. The magnitude of the effect was dependent upon the MMC concentration in the HA-DTPH-PEGDA films.

V. In Vivo Biocompatibility

Example 1

Figure 6:
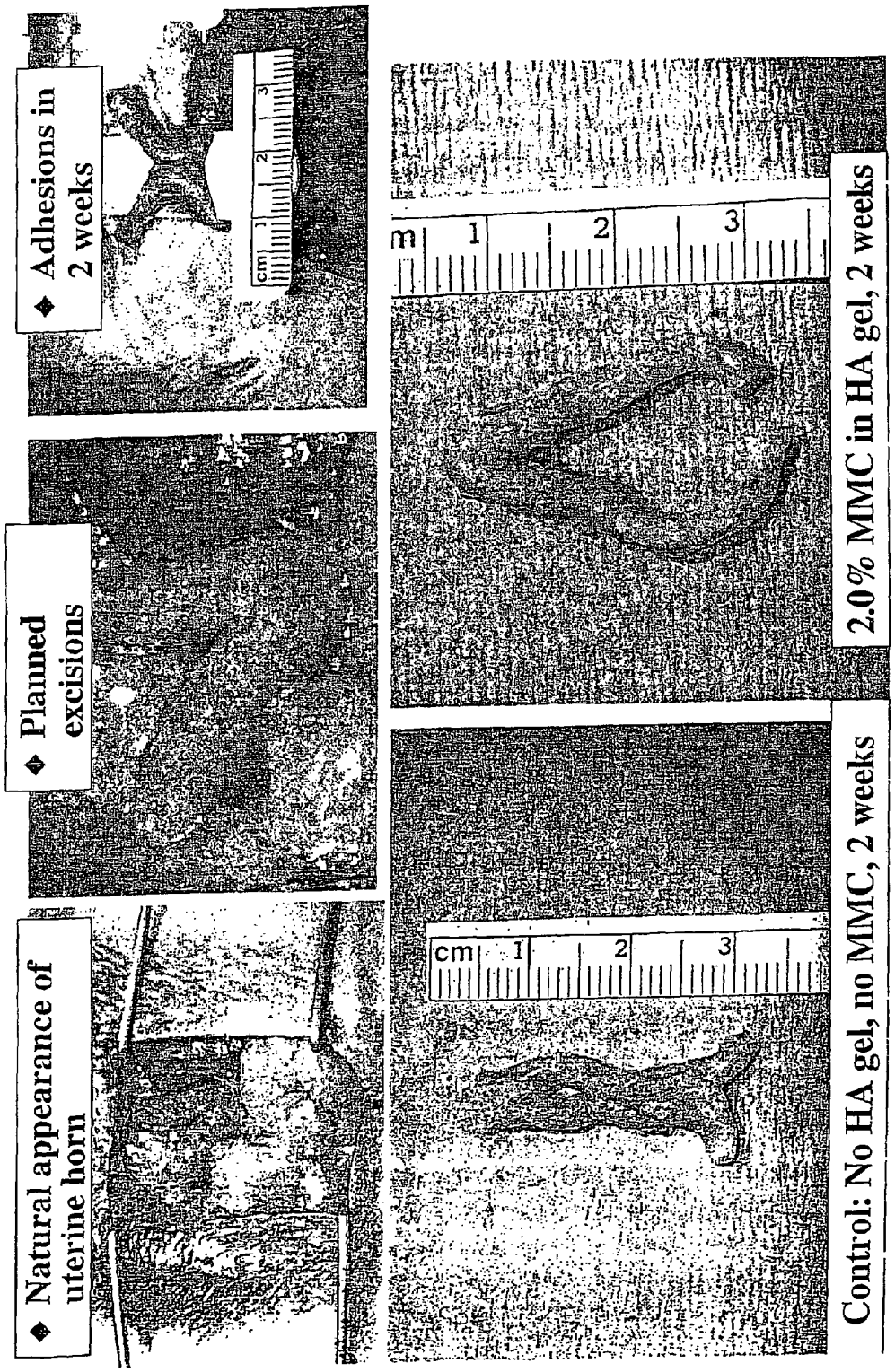
FIG. 6 shows the prevention of adhesions by crosslinked HA-DTPH-PEGDA containing MMC.

An example of the action of MMC-HA-DTPH-PEGDA is shown in FIG. 6. Using eight rats for each of four treatments, rat uterine horn adhesions were evaluated with HA gel only, and the 0.5% and 2.0% MMC gels. The severity of the adhesions were ranked on a scale from 0 to 4 (Hooker, G. D., Taylor, B. M., and Driman, D. K. (1999) Prevention of adhesion formation with use of sodium hyaluronate-based bioresorbable membrane in a rat model of ventral hernia repair with polypropylene mesh-A randomized, controlled study. Surgery 125, 211-216)). Grade 0=no adhesions; grade 1=filmy, transparent adhesions with minimal fibrous strands; grade 2=continuous fibrous adhesions; grade 4=dense adhesions. The data show statistical significance (p<0.05) for HA hydrogel treatment vs. surgical control only, and for 2.0% MMC-HA relative to HA hydrogel only.

Example 2

In addition, preliminary studies with the rabbit sinus ostia model showed that for n=8 rabbits, the HA-MMC 2.0% gel used by in situ crosslinking on the ostia, maintains a 5 mm sinus ostium with a mean for the experimental of 2.9 mm, and a mean for the control of 0.3 mm, which is statistically significant using a paired two-tailed T-test at p=0.00080 level.

Example 3

Sexually mature, non-pregnant female Wistar rats (Charles River), each weighing 250-300 g, were anesthetized by inhalation of isoflurane (2.5%) following the protocol approved by Institutional Animal Care and Use Committee at The University of Utah. After anesthesia, then the lower abdominal area was shaved, cleaned with alcohol and Betadine, and a lower ventral midline incision was made to expose the two uterine horns. Surgical injuries to the contacting serosal surfaces were created by excising a portion of the medial uterine wall musculature covering an area of 3×10 mm. The injury was 5 mm from the root of uterine horn. A single 9/0 nylon suture was placed 3 mm from the distal edge of the injured area to ensure the direct contact of the apposing injury sites on the medial aspect of the contralateral horn.

In the experimental animals, the crosslinked HA films or in situ crosslinked HA gels were placed between the two injured uterine horns. The abdominal peritoneum was closed with a single row of continuous running sutures, and the skin was approximated with interrupted sutures. On day 14 post-surgery, the animals were sacrificed by $CO_2$ inhalation, and the extent of uterine horn adhesions was assessed by estimating the length of uterine horn with adhesions (maximum 10 mm). Means and variances for each group were calculated from the average extent of adhesions for each animal. The extent (cm) of uterine horns along which adhesions formed was used as the primary outcome measurement. The presence of adhesions between the uterine horn and intraperitoneal fat and small bowel was also recorded as a binary (present or absent) parameter. After the macrographical evaluation, the samples were prepared for Masson's Trichrome staining.

To evaluate the extent of adhesions, a Student's t-test was used. Adhesion sites were compared across groups with Fisher's exact test, and a p value <0.05 was considered significant. All statistical analyses were performed with StatView (Version 5.0.1, SAS Institute Inc., Cary, N.C.).

Application of MMC-Loaded Crosslinked HA Films

Each of eight rats per experimental group received standard bilateral surgical injuries to the uterine horns. The HA films were cut into 5×12 mm rectangles and inserted between the two uterine horns at the sites of injury to completely cover the injured surfaces. A single suture was placed to prevent shifting of the film after surgical closure. The experimental groups included HA-DTPH-PEGDA films lacking MMC, and HA-DTPH-PEGDA films that contained 0.5% or 2.0% loading of MMC based on available thiol groups. Animals receiving the surgical injury but no treatment served as the no-treatment control group.

Injection of In Situ Crosslinking MMC-Loaded HA Hydrogels

Each of eight rats per experimental condition received standard surgical injuries to the two uterine horns, and were then treated as follows. First, 1 ml of a given viscous pre-gelled HA-DTPH-PEGDA (with or without MMC) was pipetted onto the surface of the injured uterine horns. Then, an additional 4 ml of the same viscous solution was injected into the peritoneal cavity through the incision in the 0.5 immediate vicinity of the uterine injuries. The experimental groups included the HA-DTPH-PEGDA in situ gel without MMC or one of the HA-DTPH-PEGDA gels with 1.25%, 0.625%, or 0.31% MMC loading. Control animals were injected with DPBS.

Efficacy of MMC-Loaded HA Films

To evaluate the anti-adhesion properties of HA films with different MMC loadings (Table 1), a rat uterine horn model was used. All experimental and control animals survived the surgical procedures, and none were excluded from the study. The extent of uterine horn adhesions was assessed by estimating the length of uterine horn that exhibited adhesions (maximum 10 mm). Means and variances for each group were calculated from the average extent of adhesions for each animal. The presence of adhesions between the uterine horn and intraperitoneal fat, and small bowel was also recorded as a yes/no response. After the macrographical evaluation, the samples were prepared for Masson's Trichrome staining.

The extent of uterine horn adhesions is shown in Table 2 and the instances of adhesion to surrounding tissues are presented in Table 3. The statistical comparisons of the groups is summarized in Table 4. First, all animals treated with a barrier hydrogel or film showed significantly reduced adhesions relative to the untreated control animals. Second, responses in both the film insertion and in situ injection methods were dependent on MMC loading. HA films with 2% MMC loading had the lowest extent of uterine horn adhesions (1.3±0.2 mm). HA films with 0.5% MMC showed an intermediate extent of uterine horn adhesions (3.5±10.4 mm), while an HA film lacking MMC still showed substantial adhesions (7.3±0.3 mm). Importantly, HA films with different MMC loadings did not significantly reduce the incidence of adhesions between the uterine horn and intraperitoneal fat or small bowel (Tables 3 and 4). No side effects were observed in the uterine horns and surrounding tissues in any of the animals in these groups.

The histology of the uterine horn injury sites was consistent with the above macrographical assessment. The treated uterine horns were distinguishable from the untreated controls (data not shown). The effects of the HA film lacking MMC were local and incomplete, which was represented by the infiltration of partial fibrous tissue and loose connective tissue between the two uterine horns. The application of the 0.5% MMC HA films or the 2.0% MMC HA film reduced fibrous tissue between the two injured uterine horns. This was attributed to the free MMC release from HA films. Without MMC loading, the HA films can only function as barriers to reduce adhesion formation. MMC dose-dependent results were obtained and no side effects were found in MMC-loaded HA films; nonetheless, it would be desirable to use the lowest fully effective MMC loading in a clinical setting.

Efficacy of MMC-Loaded In Situ Crosslinkable HA Gels

Sterilized 1.25% HA-DTPH and HA-MMC solution (with 1.25% MMC loading) were crosslinked to a theoretical extent of 50% by addition of PEGDA. To obtain lower concentrations of gel components including MMC, the HA-DTPH-MMC solution was diluted with one or three volumes of DPBS and then mixed with a PEGDA solution to achieve a theoretical extent of 50% crosslinking. These compositions are summarized in Table 1. Then, 1 ml of each viscous solution was placed (and allowed to gel) onto the surface of the injured uterine horns. An additional 4 ml of each pre-gelled solution was injected into the peritoneal cavity surrounding the injured uterine horns prior to closure of the peritoneal cavity. On day 14 post-surgery, the animals were euthanized by inhalation of $CO_2$, and the extent of uterine horn adhesions and incidence of adhesions formed to surrounding tissues was assessed.

The extent of uterine horn adhesions and the areas of adhesion from the gel injection protocols are depicted in Table 1 and Table 2, respectively. The comparison is summarized in Table 3. The injection of undiluted 1.25% MMC HA gel showed very minimal adhesions (1.4±0.3 mm), as did the 0.625% MMC HA gel (1.5±0.3 mm). In contrast, the viscous but not fully gelled 0.31% HA "gel" and was less effective in decreasing adhesions (7.3±0.6 mm). This result was similar to the HA gel that lacked MMC (7.6±0.4 mm). Nonetheless, a significantly lower adhesion extent rate was observed for these gels as compared to the DPBS treated uterine horns (9.6±0.3 mm). The data for areas of adhesion was consistent with the adhesion extent results.

Figure 7:
FIG. 7 shows the Macrographic examination of rat uterine horn adhesion (Panel A: buffer treatment; Panel B: Gel (1.25%) Panel C: Gel (0.625%); Panel D, Gel (0.31%)).
Figure 7:
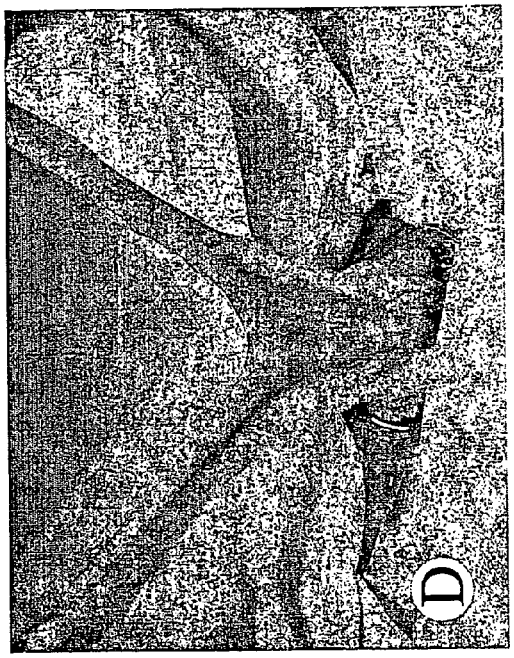
Figure 7:
Figure 7:

The macrographical examinations are illustrated in FIG. 7. Severe adhesions can be observed between the uterine horns and intraperitoneal fat, in addition to the firm adhesions formed between two uterine horns in DPBS treated animals (FIG. 7A). The formation of adhesions between the uterine horns and intraperitoneal fat was attributed to the errhysis in the procedure of superficial excision of uterine horns, i.e., light injuries on the surface of uterine horn and intraperitoneal fat caused by surgical interference and long time exposure in the air. No apparent adhesions between uterine horns and intraperitoneal fat were found in animals treated with 1.25% MMC HA gel (FIG. 7B), 0.625% MMC HA gel (FIG. 7C), 0.31% MMC HA gel (FIG. 7D). The efficacy of the 1.25% MMC HA gel and the 0.625% MMC HA gel was particularly noteworthy, as no physical barrier was actually inserted in these treatments. An unresolved gel bridging the two uterine horns and severe intraperitoneal fat atrophy were observed in the 1.25% MMC HA gel-treated animals (FIG. 7B). FIG. 7D shows that for the gels with lowest MMC loadings, the two uterine horns had abundant firm adhesions.

Figure 8:
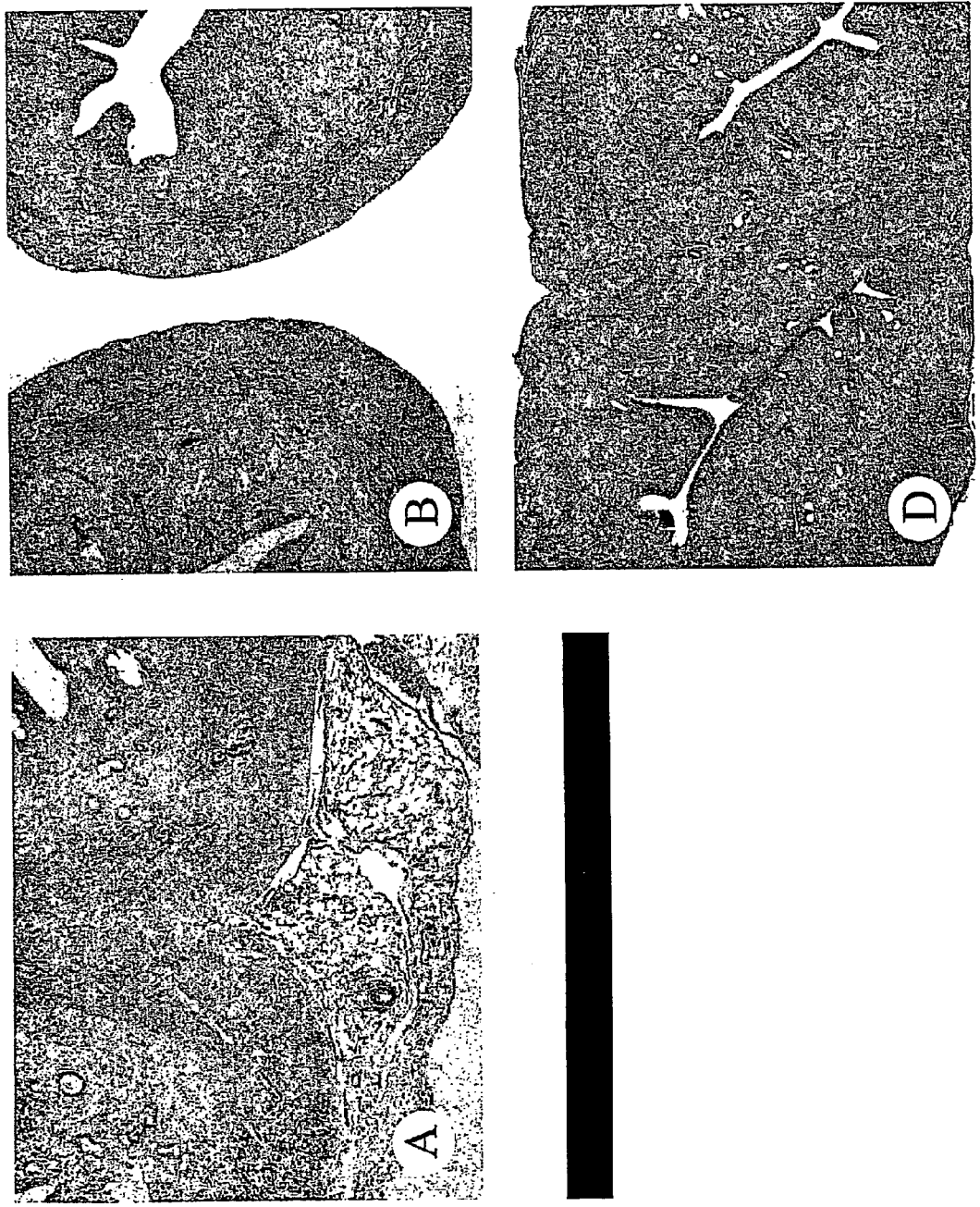
FIG. 8 shows the histological examination of rat uterine horn adhesions (Panel A: buffer treatment; Panel B: Gel (1.25%) Panel C: Gel (0.625%); Panel D, Gel (0.31%)).

The histology of the uterine horn injury sites was analyzed and found to be consistent with the above macrographical examination. In untreated animals, adhesions were found between the two uterine horns, and within the intraperitoneal fat (FIG. 8A). There was minor adhesion and some residual HA gel observed between the uterine horns in the 1.25% MMC HA gel-treated animals (FIG. 8B). The uterine horns were well separated in the 0.625% MMC HA gel-treated animals, but adhered firmly in the 0.31% MMC HA gel-treated animals (FIGS. 8C and 8D).

The efficacy of MMC-loaded HA hydrogels was highly correlated to overall concentration of the HA-DTPH used. First, with the highest concentration of HA-MMC solution (1.25%, undiluted), gelation time was short (<10 min), but a gel was obtained that was difficult to disperse and degrade. Second, after 1:1 dilution, the 0.625% MMC HA gel formed much more slowly (45 min). A thin layer of gel was evenly dispersed on the surface of the injured uterine horns and in the peritoneal cavity to form a homogeneous hydrogel membrane on the uterine horns and surrounding tissue and organs. This membrane then functioned as an in situ-produced barrier to reduce the formation of adhesions. In addition, free MMC was released from the hydrogel membrane and inhibited fibroblast proliferation. Finally, no gel formed in >2 hours when for the 1:4 dilution (0.31% MMC). The effects of this 0.31% MMC viscous sol resembled those observed for the administration of MMC solution alone in the peritoneal cavity. In this case, MMC was released and cleared rapidly, and the low MMC concentrations available were insufficient to prevent the fibroproliferative response. The intermediate concentration of 0.625% MMC with a 6.25 mg/ml HA-DTPH appeared to be optimal for the injection strategy.

In summary, both MMC-loaded HA films and HA gels were highly effective in reducing the formation of intraperitoneal post-operative adhesions. Dose-dependent results were obtained in MMC-loaded HA films. The efficacy of MMC-loaded HA gels was highly correlated to the concentration of HA-DTPH-MMC solution when preparing the hydrogel. The 0.625% MMC HA gel was shown to be fully effective in reducing post-operative adhesion formation. Compared with MMC-loaded HA films, MMC-loaded in situ crosslinkable HA gels offer a substantial advantage: the viscous solution, which gels only after 1045 min, can be locally delivered through an endoscope and can be used to prevent the adhesion formation at very specific sites that incur either severe or slight injuries to tissues and organs.

Example 4

The animal model consisted of 64 female Wistar rats (200-250 g, Charles River, Raleigh, N.C.), which were anesthetized and then subjected to a laparotomy through a 1.5-cm long incision on the lower right abdominal wall. The procedures were conducted under the supervision of The University of Utah Institutional Animal Care and Use Committee and in accordance with the standards of the National Institutes of Health guidelines (NIH Publication #85-23 Rev. 1985). HA-DTPH-MMC-PEGDA films (20.21±0.05 mg) with different MMC loadings (0%, 0.5%, and 2.0%) were inserted into the lower right abdominal cavity (16 rats per loading). An additional 16 animals underwent sham surgeries and served as the controls. At 3 days and 7 days after the insertions, eight rats from each group underwent laparotomy through a 5-mm long central incision. The abdominal cavity was instilled with 10 mL of chilled DPBS solution followed by massaging the abdomen gently for 3-5 min. Then, the DPBS solution was aspirated through a 3-mm silicon rubber tube with three small side holes on the top. The above procedures were repeated twice, and the three aspirates were pooled from each animal for leukocyte differential counts. Finally, the rats were euthanized in a $CO_2$ chamber, and the films with surrounding tissue were excised for histological examination.

Leukocyte differential counts. Peritoneal fluid leukocyte differential counts were made from slides from aliquots with a cytocentrifuge (Centra CL2, IEC, San Antonio, Tex.). The slides were air-dried and stained with a Wright-Giemsa stain (Fisher). The peritoneal fluid leukocyte number was determined by counting the cells in a standard clinical hemocytometer.

Histology. The films with surrounding tissues were excised and fixed with 10% formalin, embedded in paraffin, sectioned to 2-3 μm thickness with a microtome at three different distances from the surface, and stained with periodic acid-Schiff (PAS) reagent. The thickness of fibrous tissue surrounding the films was measured using Image-Pro Plus 4.0 (Symantec, Corporation, Cupertino, Calif.). Three sections from each sample and sixteen points from each section were measured.

Statistical analysis. Anaylsis of variance (ANOVA) was applied using StatView software (SAS Institute Inc., Cary, N.C.) to determine differences in statistical significance. Values of $p<0.05$ were deemed to be significantly different.

Figure 11:
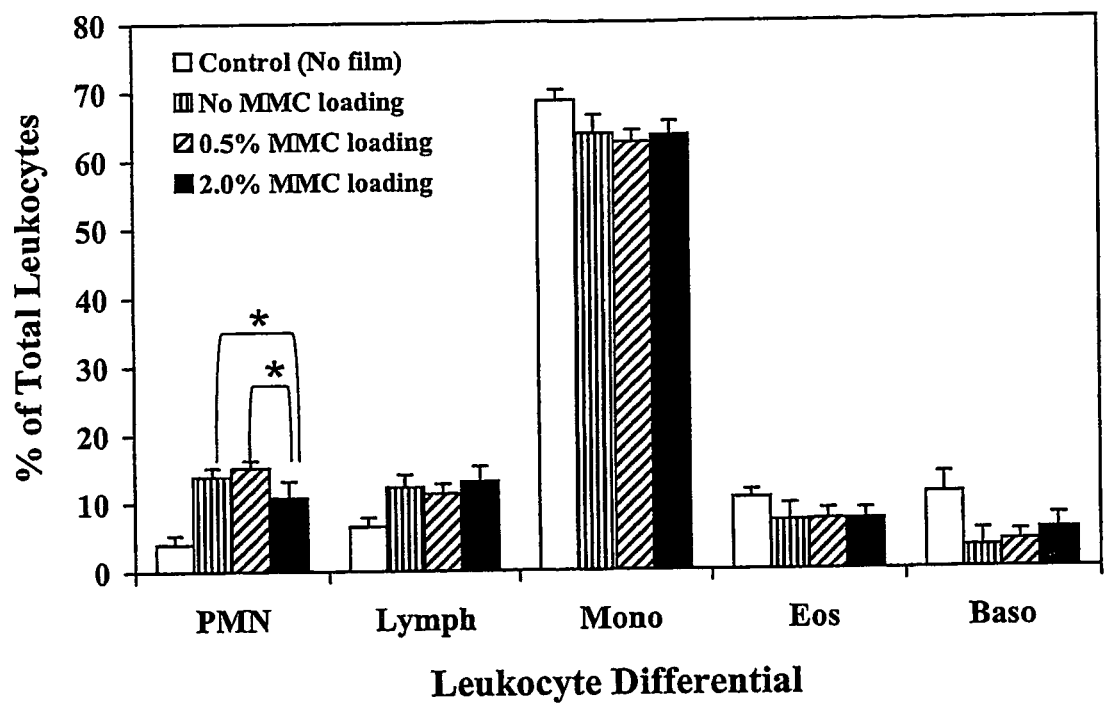
FIG. 11 shows leukocyte differential in peritoneal fluid in the presence of HA-DTPH-MMC-PEGDA films.

To investigate the biocompatibility of the HA-DTPH-MMC-PEGDA films, HA films with different MMC loadings were studied in vivo by inserting the films into a rat peritoneal cavity and evaluating the cell population in the peritoneal fluid on day 3 and day 7 post implantation. All the cells present in the peritoneal fluid were morphologically identifiable as leukocytes, and the differential counts on day 3 are depicted in FIG. 11 (Key to FIG. 11: PMN=polymorphonuclear cells; Lymph=lymphocytes; Mono=mononuclear cells include both monocytes and macrophages; Eos=eosinophils; and Baso=basophils). Films with 0.5% MMC showed higher PMN relative to films without MMC ($p<0.001$), while films with 2% MMC showed lower PMN than both 0.5% MMC ($p<0.001$) and no-MMC films $p<0.05$). Only PMN showed a slight but significant difference relative to the no-film control. The most readily identifiable change in the peritoneal fluid was observed in the polymorphonuclear (PMN) leukocytes. No other significant changes were observed for the lymphocyte or mononuclear cell populations in any of the experimental groups. The HA-DTPH-PEGDA films lacking MMC and HA-DTPH-MMC-PEGDA films with 0.5% and 2.0% MMC induced a modest augmentation in PMN compared to the no-film control, which was likely due to degradation of the film. Although the degradation rate was very slow, the leukocyte response caused by degradation fragments appeared dominant relative to the effect from released MMC. Nonetheless, the MMC released from the films with 2.0% MMC loading significantly lowered the average PMN number (11%) when compared to either the HA-DTPH-PEGDA films lacking MMC (14%) or the HA-DTPH-MMC-PEGDA with 0.5% MMC (15%). This can be attributed to the cytotoxic effects of MMC at higher concentrations. By day 7, the PMN numbers from all film insertion groups were not significantly different from those for the control group in which no films had been inserted (data not shown).

Figure 12:
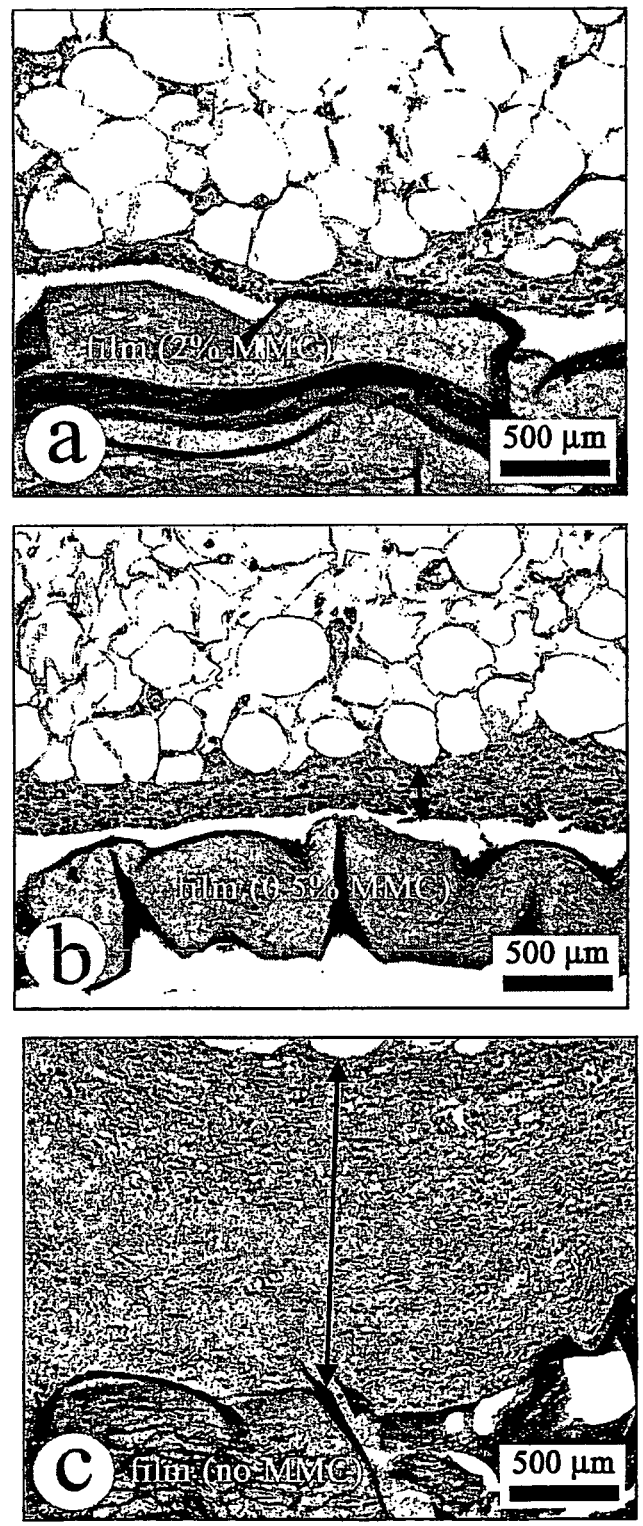
FIG. 12 shows the histology of peritoneal tissue for HA-DTPH-MMC-PEGDA at day 7 post-implantation as visualized by PAS staining.

The films and surrounding tissues were excised after day 7 for histological examination. No obvious inflammatory response was observed in any of the groups (FIG. 12: (a) HA-DTPH-MMC-PEGDA film with 2% MMC; (b) HA-DTPH-MMC-PEGDA film with 0.5% MMC loading; and (c) HA-DTPH-PEGDA film alone (no MMC). Scale bar: 500 μm. Two-headed arrows indicate the length of fibrous tissue measured. Asterisks indicate statistically significant differences ($p<0.05$)). Significant differences in fibrous tissue thickness surrounding the films was observed using Image-Pro Plus 4.0 software. As expected, the films with 2% MMC loading had thinner fibrous tissue formation (FIG. 12a and Table 5), while the films with 0.5% MMC had thicker fibrous tissue formation (FIG. 12b and Table 5). The films lacking MMC exhibited the thickest fibrous tissue (FIG. 12c and Table 5). These results revealed that, as expected from the in vitro culture data, the HA-DTPH-MC-PEGDA films did inhibit fibroblast proliferation in a dose-dependent manner. Taken together, these data establish that HA-DTPH-PEGDA films lacking MMC or with two MMC loadings have good biocompatibility, but that HA-DTPH-MMC-PEGDA with 0.5% MMC would likely be optimal for use in the prevention of post-surgical adhesions.

Throughout this application, various publications are referenced. The disclosures of these publications in their entireties are hereby incorporated by reference into this application in order to more fully describe the compounds, compositions and methods described herein.

Various modifications and variations can be made to the compounds, compositions and methods described herein. Other aspects of the compounds, compositions and methods described herein will be apparent from consideration of the specification and practice of the compounds, compositions and methods disclosed herein. It is intended that the specification and examples be considered as exemplary.

TABLE 1

Compositions of biomaterials

| Abbreviated form | Film | HA-DTPH concentration[a] | Volume of film prepared (mm) | Volume of film used in each animal (mm) | MMC loading | Total MMC used in each animal (µg) |
|---|---|---|---|---|---|---|
| HA Film (0) | HA-DTPH-PEDA | 1.25% | 20 × 20 × 0.1 | 5 × 12 × 0.1 | 0% | 0 |
| HA Film (0.5%) | HA-DTPH-MMC-PEDDA (0.5% MMC loading) | 1.25% | 20 × 20 × 0.1 | 5 × 12 × 0.1 | 0.5% | 4.86 |
| HA Film (2.0%) | HA-DTPH-MMC-PEDDA (2% MMC loading) | 1.25% | 20 × 20 × 0.1 | 5 × 12 × 0.1 | 2% | 19.44 |

| | Gel | HA-DTPH concentration | MMC concentration in gel (µg/ml) | Volume of gel used in each animal (ml) | MMC loading | Total MMC used in each animal (µg) |
|---|---|---|---|---|---|---|
| HA Gel (0) | HA-DTPH-PEGDA | 1% | 0 | 5 | 0 | 0 |
| HA Gel (0.31%) | HA-DTPH-MMC-PEGDA (0.31% MMC loading) | 0.25% | 10.1 | 5 | 0.31% | 50.62 |
| HA Gel (0.625%) | HA-DTPH-MMC-PEGDA (0.625% MMC loading) | 0.5% | 20.3 | 5 | 0.625% | 101.3 |
| HA Gel (1.25%) | HA-DTPH-MMC-PEGDA (1.25% MMC loading) | 1% | 40.5 | 5 | 1.25% | 202.3 |

[a]HA-DTPH concentration for film preparation

TABLE 2

Efficacy of HA films and gels for extent of adhesions

| Treatment group[†] | Extent of Adhesions (mm) |
|---|---|
| Insertion of Sterilized Films | |
| Untreated | 9.5 ± 0.4 |
| HA Film (0) | 7.3 ± 0.3 |
| HA Film (0.5%)[†] | 3.5 ± 0.4 |
| HA Film (2.0%) | 1.3 ± 0.2 |
| Injection of in situ Crosslinkable Gels | |
| Buffer | 9.6 ± 0.3 |
| HA Gel (0) | 7.6 ± 0.4 |
| HA Gel (1.25%) | 1.4 ± 0.3 |
| HA Gel (0.625%) | 1.5 ± 0.3 |
| HA Gel (0.31%) | 7.3 ± 0.6 |

Values are means ± SD for n = 8 rats per experimental set.
[†]See Table 1 for compositions of materials

TABLE 3

Locations of Abdominal Adhesions (n = 8 animals per set)

| | Adhesion site | |
|---|---|---|
| Treatment group | Uterine horn-intraperitoneal fat | Uterine horn-small bowel |
| Insertion of Sterilized Films | | |
| Untreated | Yes = 8 / No = 0 | Yes = 7 / No = 1 |
| HA (0) | Yes = 7 / No = 1 | Yes = 8 / No = 0 |
| HA Film (0.5%) | Yes = 7 / No = 1 | Yes = 7 / No = 1 |
| HA Film (2.0%) | Yes = 7 / No = 1 | Yes = 7 / No = 1 |
| Injection of in situ Crosslinkable Gels | | |
| Buffer | Yes = 7 / No = 1 | Yes = 8 / No = 0 |
| HA Gel (0) | Yes = 5 / No = 3 | Yes = 3 / No = 5 |
| HA Gel (1.25) | Yes = 0 / No = 8 | Yes = 1 / No = 7 |
| HA Gel (0.625%) | Yes = 1 / No = 7 | Yes = 0 / No = 8 |
| HA Gel (0.31%) | Yes = 3 / No = 5 | Yes = 5 / No = 3 |

TABLE 4

Statistical Comparisons Between Experimental Groups. The extent of adhesion was compared across groups with Student's t-test, and adhesion sites were compared with Fisher's exact test. A P value < 0.05 was considered significant.

| Comparison | P value (extent) | P value (adhesion sites) |
|---|---|---|
| Among inserted films | | |
| HA (0) vs. Untreated | P < 0.0001 | P = 0.5452 |
| HA Films (0.5% vs. 0) | P < 0.0001 | P = 0.7851 |
| HA Films (2.0% vs. 0.5%) | P < 0.0001 | N/A |
| Among injected in situ crosslinkable gels | | |
| HA Gel vs. buffer | P < 0.0001 | P = 0.035 |
| HA Gels (1.25% vs. 0) | P < 0.0001 | P = 0.035 |
| HA Gels (0.625 vs. 0) | P < 0.0001 | P = 0.0469 |
| HA Gels (0.625 vs. 1.25%) | P = 0.73 | P = 0.5452 |
| HA Gels (0.31% vs. no 1.25%) | P < 0.0001 | P = 0.0469 |
| HA Gel (0.31%) vs. buffer | P < 0.0001 | P = 0.0469 |
| Between pre-formed films and injectable gels | | |
| HA Gel (1.25%) Gel vs. HA Film (2.0%) | P = 0.30 | P = 0.006 |
| HA Gel (0.625%) vs. HA Film (2.0%) | P = 0.18 | P = 0.018 |
| HA Gel (0.31%) vs. HA Film (2.0%) | P < 0.0001 | P = 0.0362 |

TABLE 5

Comparison of fibrous tissue thickness formed in vivo

| Film | Thickness of fibrous tissue (μm) | Paired comparison | p value |
|---|---|---|---|
| HA-DTPH-MMC-PEGDA (2% MMC) | 144.2 ± 40.4 | 2% MMC vs. 0.5% MMC | p < 0.001 |
| HA-DTPH-MMC-PEGDA (0.5% MMC) | 261.0 ± 69.3 | 2% MMC vs. no MMC | p < 0.001 |
| HA-DTPH-PEGDA (no MMC) | 1605.0 ± 123.6 | 0.5% MMC vs. no MMC | p < 0.001 |

What is claimed:

1. A composite comprising (1) a first compound comprising, the reaction product between a thiolated compound having at least one SH group with at least one first anti-adhesion compound having at least one thiol-reactive electrophilic functional group, and (2) a first prohealing compound, wherein the thiolated compound comprises the formula III

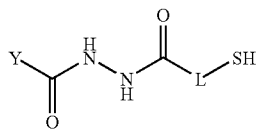

wherein
L is a polyalkylene group, a polyether group, a polyamide group, a polyimino group, a polyester, an aryl group, or a polythioether group; and
Y is a residue of carboxymethylcellulose, hyaluronan, or a chemically modified-derivative of hyaluronan;
the first anti-adhesion compound comprises an anti-cancer drug, an anti-proliferative drug, a PKC inhibitor, an ERK or MAPK inhibitor, a cdc inhibitor, an anti-mitotic, a DNA intercalator, a covalent modifier of DNA, an anti-inflammatory compound, or an inhibitor of PI3 kinase; and
the first prohealing compound is a polysaccharide selected from the group consisting of chondroitin sulfate, dermatan, heparan, heparin, dermatan sulfate, heparan sulfate, alginic acid, pectin, carboxymethylcellulose, and hyaluronan.

2. The composite of claim 1, wherein Y is a residue of hyaluronan.

3. The composite of claim 1, wherein L is $CH_2CH_2$ or $CH_2CH_2CH_2$.

4. The composite of claim 1, wherein the first anti-adhesion compound is mitomycin C.

5. The composite of claim 1, wherein the thiol-reactive electrophilic functional group on the first anti-adhesion compound comprises an electron-deficient vinyl group.

6. The composite of claim 1, wherein the wherein the electron-deficient vinyl group comprises an acrylate group, a methacrylate group, an acrylamide, or a methacrylamide.

7. The composite of claim 1, wherein the first anti-adhesion compound comprises mitomycin C having at least one acrylate group.

8. The composite of claim 1, wherein the first compound comprises the reaction product between the thiolated compound having the formula III

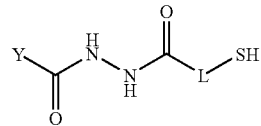

wherein
Y comprises a residue of carboxymethylcellulose, hyaluronan, or a chemically modified-derivative of hyaluronan, and
L comprises $CH_2CH_2$ or $CH_2CH_2CH_2$, and
a first anti-adhesion compound comprising mitomycin C having at least one acrylate group.

9. The composite of claim 1, further comprising the reaction product between the first anti-adhesion compound and the thiolated compound with a crosslinker.

10. The composite of claim 9, wherein the crosslinker comprises the formula V

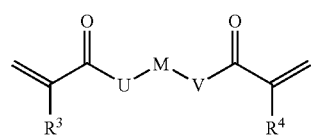

wherein
$R^3$ and $R^4$ comprise, independently, hydrogen or lower alkyl;
U and V comprise, independently, O or $NR^5$, wherein $R^5$ comprises hydrogen or lower alkyl; and
M comprises a polyalkylene group, a polyether group, a polyamide group, a polyimino group, a polyester, an aryl group, or a polythioether group.

11. The composite of claim 9, wherein the compound having the formula V comprises polyethylene glycol diacrylate.

12. The composite of claim 1, wherein the composite further comprises a second anti-adhesion compound that is not covalently bonded to the thiolated compound, wherein the first anti-adhesion compound and the second anti-adhesion compound are different, wherein the second anti-adhesion compound comprises an anti-cancer drug, an anti-proliferative drug, a PKC inhibitor, an ERK or MAPK inhibitor, a cdc inhibitor, an antimitotic, a DNA intercalator, a covalent modifier of DNA, an anti-inflammatory compound, or an inhibitor of PI3 kinase.

13. The composite of claim 1, wherein the composite further comprises a second prohealing compound, wherein the second prohealing compound is different from the first prohealing compound, and wherein the second prohealing compound comprises a growth factor.

14. The composite of claim 13, wherein the growth factor comprises a nerve growth promoting substance, a nerve growth factor, a hard or soft tissue growth promoting agent, human growth hormone, a colony stimulating factor, a bone morphogenic protein, a platelet-derived growth factor, an insulin-derived growth factor, a transforming growth factor-alpha, a transforming growth factor-beta, an epidermal growth factor, a fibroblast growth factor, a vascular endothelial growth factor, a keratinocyte growth factor, or a dried bone material.

15. The composite of claim 1, wherein the first compound is crosslinked with itself and/or the prohealing compound.

16. A pharmaceutical composition comprising a pharmaceutically-acceptable compound and the composite of claim 1.

17. A kit comprising
(1) a first compound comprising the reaction product between a thiolated compound having at least one SH group with at least one first anti-adhesion compound having at least one thiol-reactive electrophilic functional group, and (2) a first prohealing compound,
wherein the thiolated compound comprises the formula III

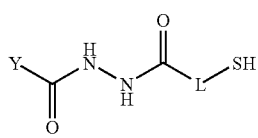

wherein
L is a polyalkylene group, a polyether group, a polyamide group, a polyimino group, a polyester, an aryl group, or a polythioether group; and
Y is a residue of carboxymethylcellulose, hyaluronan, or a chemically modified-derivative of hyaluronan;
the first anti-adhesion compound comprises an anti-cancer drug, an anti-proliferative drug, a PKC inhibitor, an ERK or MAPK inhibitor, a cdc inhibitor, an anti-mitotic, a DNA intercalator, a covalent modifier of DNA, an anti-inflammatory compound, or an inhibitor of PI3 kinase; and
the first prohealing compound is a polysaccharide selected from the group consisting of chondroitin sulfate, dermatan, heparan, heparin, dermatan sulfate, heparan sulfate, alginic acid, pectin, carboxymethylcellulose, and hyaluronan.

18. An article comprising the composite of claim 1.

19. The article of claim 18, wherein the article comprises a gel, a bead, a sponge, a film, a mesh, or a matrix.

20. The article of claim 18, wherein the composite comprises a laminate.

21. The article of claim 20, wherein the laminate comprises a first layer and a second layer, wherein (1) the first layer comprises a first compound having a first surface and a second surface, and (2) the second layer comprises a first prohealing compound, wherein the second layer has a first surface and a second surface, wherein the first surface of the first layer is adjacent to the first surface of the second layer.

22. The composite of claim 21, wherein the laminate further comprises a third layer comprising a second prohealing compound, wherein the third layer has a first surface and a second surface, wherein the first surface of the third layer is adjacent to the second surface of the first layer, and the second prohealing compound is a polysaccharide selected from the group consisting of chondroitin sulfate, dermatan, heparan, heparin, dermatan sulfate, heparan sulfate, alginic acid, pectin, carboxymethylcellulose, and hyaluronan.

23. A compound comprising the reaction product between a thiolated compound having at least one SH group with at least one first anti-adhesion compound having at least one thiol-reactive electrophilic functional group, wherein the thiolated compound comprises the formula III

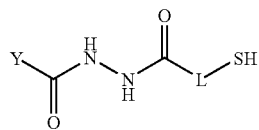

wherein
L is a polyalkylene group, a polyether group, a polyamide group, a polyimino group, a polyester, an aryl group, or a polythioether group; and
Y is a residue of carboxymethylcellulose, hyaluronan, or a chemically modified-derivative of hyaluronan; and
the first anti-adhesion compound comprises an anti-cancer drug, an anti-proliferative drug, a PKC inhibitor, an ERK or MAPK inhibitor, a cdc inhibitor, an anti-mitotic, a DNA intercalator, a covalent modifier of DNA, an anti-inflammatory compound, or an inhibitor of PI3 kinase.

24. The compound of claim 23, wherein L is $CH_2CH_2$ or $CH_2CH_2CH_2$.

25. The compound of claim 23, wherein the first anti-adhesion compound c is mitomycin C.

26. The compound of claim 23, wherein the thiol-reactive electrophilic functional group on the first anti-adhesion compound comprises an electron-deficient vinyl group.

27. The compound of claim 26, wherein the wherein the electron-deficient vinyl group comprises an acrylate group, a methacrylate group, an acrylamide, or a methacrylamide.

28. The compound of claim 23, wherein the first anti-adhesion compound comprises mitomycin C having at least one acrylate group.

29. The compound of claim 23, wherein the first compound comprises the reaction product between a thiolated compound comprising the formula III

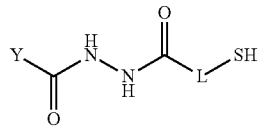

wherein
Y is a residue of carboxymethylcellulose, hyaluronan, or a chemically modified-derivative of hyaluronan, and
L is $CH_2CH_2$ or $CH_2CH_2CH_2$, and
a first anti-adhesion compound comprising mitomycin C having at least one acrylate group.

30. The compound of claim 23, further comprising the reaction product between the first anti-adhesion compound and thiolated compound with a crosslinker.

31. The compound of claim 30, wherein the crosslinker comprises the formula V

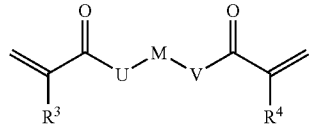

wherein
- $R^3$ and $R^4$ comprise, independently, hydrogen or lower alkyl;
- U and V comprise, independently, O or $NR^5$, wherein $R^5$ comprises hydrogen or lower alkyl; and
- M comprises a polyalkylene group, a polyether group, a polyamide group, a polyimino group, a polyester, an aryl group, or a polythioether group.

32. The compound of claim 31, wherein the compound having the formula V comprises polyethylene glycol diacrylate.

33. A method for reducing or inhibiting adhesion of two tissues in a surgical wound in a subject, comprising contacting the wound of the subject with the composite of claim 1.

34. The method of claim 33, wherein the surgical wound is produced from cardiosurgery, articular surgery, abdominal surgery, thoracic surgery, surgery in the urogenital region, nerve surgery, tendon surgery, laparascopic surgery, pelvic surgery, oncological surgery, sinus and craniofacial surgery, ENT surgery, ophthalmological surgery, or a procedure involving spinal dura repair.

35. The method of claim 33, wherein the composite is preformed prior to contacting the wound.

36. The method of claim 33, wherein the composite is formed in situ upon contacting the wound.

37. The method of claim 33, wherein the composite is a laminate, wherein the laminate comprises a first layer and a second layer, wherein (1) the first layer comprises a first compound having a first surface and a second surface, and (2) the second layer comprises a first prohealing compound, wherein the second layer has a first surface and a second surface, wherein the first surface of the first layer is adjacent to the first surface of the second layer.

38. The method of claim 37, wherein the laminate is wrapped around a skeletal structure, wherein the second surface of the first layer of the laminate is in contact with the skeletal structure.

39. The method of claim 37, wherein the skeletal structure is bone, cartilage, or a tendon.

40. A method for improving wound healing in a subject in need of such improvement, comprising contacting the wound of the subject with the composite of claim 1.

* * * * *